US011839587B1

(12) United States Patent
Swoboda et al.

(10) Patent No.: US 11,839,587 B1
(45) Date of Patent: Dec. 12, 2023

(54) SYSTEMS, DEVICES, AND METHODS FOR AMBULATORY RESPIRATION ASSISTANCE

(71) Applicant: RightAir, Inc., Philadelphia, PA (US)

(72) Inventors: Michal Swoboda, Philadelphia, PA (US); Marek Swoboda, Philadelphia, PA (US)

( * ) Notice: Subject to any disclaimer, the term of this patent is extended or adjusted under 35 U.S.C. 154(b) by 0 days.

(21) Appl. No.: 18/164,271

(22) Filed: Feb. 3, 2023

(51) Int. Cl.
*A61H 31/02* (2006.01)
*A61M 16/20* (2006.01)
*A61M 16/00* (2006.01)

(52) U.S. Cl.
CPC ......... *A61H 31/02* (2013.01); *A61M 16/0066* (2013.01); *A61M 16/022* (2017.08); *A61M 16/208* (2013.01); *A61H 2201/1207* (2013.01); *A61H 2201/1246* (2013.01); *A61H 2201/1619* (2013.01); *A61H 2201/1647* (2013.01); *A61H 2201/5056* (2013.01); *A61H 2201/5071* (2013.01); *A61H 2201/5087* (2013.01); *A61H 2230/425* (2013.01)

(58) Field of Classification Search
CPC ............ A61H 31/02; A61H 2201/1207; A61H 2201/1246; A61H 2201/1619; A61H 2201/1647; A61H 2201/5056; A61H 2201/5071; A61H 2201/5087; A61H 2230/425; A61M 16/0066; A61M 16/022; A61M 16/208
See application file for complete search history.

(56) References Cited

U.S. PATENT DOCUMENTS

| 1,834,580 A | 12/1931 | Philip et al. |
| 2,065,982 A | 12/1936 | August |
| 2,079,952 A | 5/1937 | Henrik |

(Continued)

FOREIGN PATENT DOCUMENTS

| CA | 2261024 C | 4/2007 |
| FR | 1051708 A | 1/1954 |

(Continued)

OTHER PUBLICATIONS

Extended European Search Report for European Patent Application No. 19900268.4, dated Aug. 22, 2022, 9 pages.

(Continued)

*Primary Examiner* — Kendra D Carter
*Assistant Examiner* — Arielle Wolff
(74) *Attorney, Agent, or Firm* — COOLEY LLP

(57) ABSTRACT

Systems and devices described herein provide respiration assistance to users who have difficulty breathing on their own, and include a cuirass configured to be coupled to a thorax of the user and a ventilator fluidically coupled to the cuirass. The ventilator includes a housing, a pump including an inlet and outlet, a valve, an actuator, and a controller in communication with the actuator. The controller is configured to cause the actuator to: move the valve into a first configuration in which a first flow path of the valve fluidically couples the outlet to the cuirass and a second flow path of the valve fluidically couples the inlet to an external environment during exhalation and move the valve into a second configuration in which the first flow path fluidically (Continued)

couples the inlet to the cuirass and the second flow path fluidically couples the outlet to the internal volume during inhalation.

15 Claims, 21 Drawing Sheets

(56) References Cited

U.S. PATENT DOCUMENTS

| | | | |
|---|---|---|---|
| 2,287,939 A | 6/1942 | Kraft | |
| 2,309,361 A | 1/1943 | Terhaar | |
| 2,456,724 A | 12/1948 | Mullikin | |
| 2,466,108 A | 4/1949 | Huxley | |
| 2,480,980 A | 9/1949 | Terhaar | |
| 2,529,258 A | 11/1950 | Gonzalez | |
| 2,629,372 A | 2/1953 | Wallin | |
| 2,699,163 A | 1/1955 | Engstrom | |
| 2,759,474 A | 8/1956 | Kling | |
| 2,825,327 A | 3/1958 | James | |
| 3,078,842 A | 2/1963 | Gray | |
| 3,368,550 A | 2/1968 | Harry | |
| 3,961,626 A | 6/1976 | Houchen et al. | |
| 4,257,407 A | 3/1981 | Macchi | |
| 4,844,390 A | 7/1989 | Duke | |
| 4,881,527 A | 11/1989 | Lerman | |
| 4,945,899 A | 8/1990 | Sugiyama et al. | |
| 4,971,042 A | 11/1990 | Lerman | |
| 5,076,259 A | 12/1991 | Hayek | |
| 5,222,491 A | 6/1993 | Thomas | |
| 5,573,498 A | 11/1996 | Hayek | |
| 5,820,572 A | 10/1998 | Palmer | |
| 6,345,618 B1 | 2/2002 | Hayek | |
| 6,488,641 B2 | 12/2002 | Hansen | |
| 6,910,479 B1 | 6/2005 | Van Brunt | |
| 6,916,298 B2 | 7/2005 | Vanbrunt et al. | |
| 7,278,978 B1 | 10/2007 | Hansen et al. | |
| 7,316,658 B2 | 1/2008 | Gagne | |
| 7,374,550 B2 | 5/2008 | Hansen et al. | |
| 7,425,203 B2 | 9/2008 | Van Brunt et al. | |
| 7,491,182 B2 | 2/2009 | Van Brunt | |
| 7,582,065 B2 | 9/2009 | Van Brunt et al. | |
| 7,615,017 B2 | 11/2009 | Van Brunt et al. | |
| 7,744,547 B2 | 6/2010 | Jiang et al. | |
| 7,785,280 B2 | 8/2010 | Kivisto | |
| 8,038,633 B2 | 10/2011 | Van Brunt et al. | |
| 8,197,428 B2 | 6/2012 | Helgeson et al. | |
| 8,202,237 B2 | 6/2012 | Helgeson et al. | |
| 8,540,653 B2 | 9/2013 | Baldauf et al. | |
| 8,578,939 B1 | 11/2013 | Kimani Mwangi et al. | |
| 8,708,937 B2 | 4/2014 | Van Brunt et al. | |
| 9,289,350 B2 | 3/2016 | Helgeson et al. | |
| 9,572,743 B2 | 2/2017 | Ikeler et al. | |
| 9,724,486 B2 | 8/2017 | Lee et al. | |
| 9,744,097 B2 | 8/2017 | DeVlleger et al. | |
| 9,795,752 B2 | 10/2017 | Birnkrant et al. | |
| 9,895,287 B2 | 2/2018 | Shockley, Jr. et al. | |
| 9,907,725 B2 | 3/2018 | Shockley, Jr. et al. | |
| 9,956,134 B2 | 5/2018 | Shockley, Jr. et al. | |
| 10,016,335 B2 | 7/2018 | Hansen et al. | |
| 10,105,281 B1 | 10/2018 | Costella | |
| 10,251,810 B2 | 4/2019 | Shockley, Jr. et al. | |
| 10,292,890 B2 | 5/2019 | DeVliegar et al. | |
| 10,478,375 B2 | 11/2019 | Antros | |
| 10,561,576 B2 | 2/2020 | Glenn et al. | |
| 10,610,446 B2 | 4/2020 | Shockley, Jr. et al. | |
| 10,722,425 B2 | 7/2020 | Shockley, Jr. et al. | |
| 10,765,591 B2 | 9/2020 | Antros | |
| 10,814,082 B2 | 10/2020 | Birnkrant et al. | |
| 10,874,582 B2 | 12/2020 | Shockley, Jr. et al. | |
| 10,940,083 B2 | 3/2021 | Chen et al. | |
| 10,952,918 B2 | 3/2021 | Palmer | |
| 10,973,734 B2 | 4/2021 | Shockley, Jr. et al. | |
| 11,013,659 B2 | 5/2021 | Shockley, Jr. et al. | |
| 11,052,019 B2 | 7/2021 | Freeman et al. | |
| 11,484,465 B2 | 11/2022 | Kavanagh et al. | |
| 11,554,076 B2 | 1/2023 | Palmer et al. | |
| 2002/0078958 A1 | 6/2002 | Stenzler | |
| 2004/0094216 A1* | 5/2004 | Wagner | F16K 11/0743 137/625.46 |
| 2004/0158177 A1 | 8/2004 | Van Brunt et al. | |
| 2007/0276299 A1 | 11/2007 | Jiang et al. | |
| 2008/0000477 A1 | 1/2008 | Huster et al. | |
| 2008/0115786 A1 | 5/2008 | Sinderby et al. | |
| 2008/0167586 A1 | 7/2008 | Baldauf et al. | |
| 2009/0171256 A1 | 7/2009 | Fiorina | |
| 2011/0098741 A1 | 4/2011 | Pfeiffer | |
| 2012/0174275 A1 | 7/2012 | Carlson | |
| 2014/0113753 A1 | 4/2014 | Craig | |
| 2015/0045704 A1 | 2/2015 | Lurie et al. | |
| 2016/0324722 A1 | 11/2016 | Sinderby et al. | |
| 2016/0349738 A1 | 12/2016 | Sisk | |
| 2017/0209334 A1 | 7/2017 | Francois et al. | |
| 2017/0304147 A1 | 10/2017 | Glenn et al. | |
| 2019/0105225 A1* | 4/2019 | Brenner | A61H 23/0245 |
| 2020/0121551 A1 | 4/2020 | Radbourne | |
| 2020/0206454 A1 | 7/2020 | Lurie et al. | |
| 2020/0268601 A1 | 8/2020 | Antros | |
| 2020/0398018 A1* | 12/2020 | Endo | A61M 16/0875 |
| 2021/0008309 A1 | 1/2021 | Birnkrant et al. | |
| 2021/0059900 A1 | 3/2021 | Halperin et al. | |
| 2021/0137779 A1 | 5/2021 | Ayu et al. | |
| 2021/0177690 A1 | 6/2021 | Palmer | |
| 2021/0187223 A1 | 6/2021 | Sing et al. | |
| 2021/0283008 A1 | 9/2021 | Shockley, Jr. et al. | |
| 2021/0346623 A1 | 11/2021 | Sinderby et al. | |
| 2022/0054353 A1 | 2/2022 | Swoboda et al. | |
| 2022/0071841 A1 | 3/2022 | Bull | |

FOREIGN PATENT DOCUMENTS

| | | | |
|---|---|---|---|
| KR | 101731049 B1 | 4/2017 | |
| KR | 101796251 B1 | 11/2017 | |
| RU | 2626305 C1 | 7/2017 | |
| TW | 365537 B | 8/1999 | |
| TW | M610600 U | 4/2021 | |
| WO | WO-9639112 A1 | 12/1996 | |
| WO | WO-2005039679 A1 | 5/2005 | |
| WO | WO-2005070488 A1 | 8/2005 | |
| WO | WO-2017081352 A1 | 5/2017 | |
| WO | WO-2017165359 A1 | 9/2017 | |
| WO | WO-2020076821 A1 | 4/2020 | |
| WO | WO-2020131736 A1 | 6/2020 | |
| WO | WO-2021222062 A1 | 11/2021 | |
| WO | WO-2022066162 A1 | 3/2022 | |

OTHER PUBLICATIONS

International Preliminary Report on Patentability for Application No. PCT/US2017/023326, dated Oct. 4, 2018, 10 pages.
International Preliminary Report on Patentability for Application No. PCT/US2019/066603, dated Jul. 1, 2021, 12 pages.
International Search Report and Written Opinion for Application No. PCT/US2017/023326, dated Jun. 9, 2017, 10 pages.
International Search Report and Written Opinion for Application No. PCT/US2019/066603, dated Mar. 3, 2020, 14 pages.
U.S. Appl. No. 16/086,892: Office Action, dated Aug. 5, 2021; 15 pages.
U.S. Appl. No. 16/086,892: Office Action, dated Feb. 16, 2022; 17 pages.
U.S. Appl. No. 16/086,892: Office Action, dated Jun. 24, 2022; 17 pages.
U.S. Appl. No. 16/086,892: Office Action, dated Mar. 2, 2023; 18 pages.

* cited by examiner

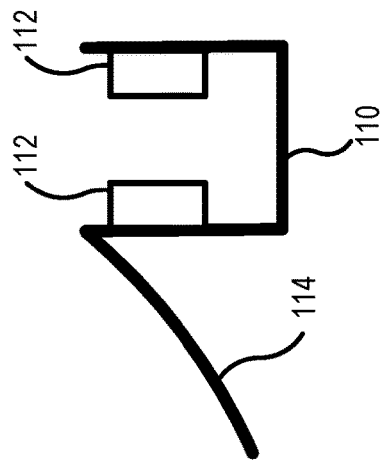
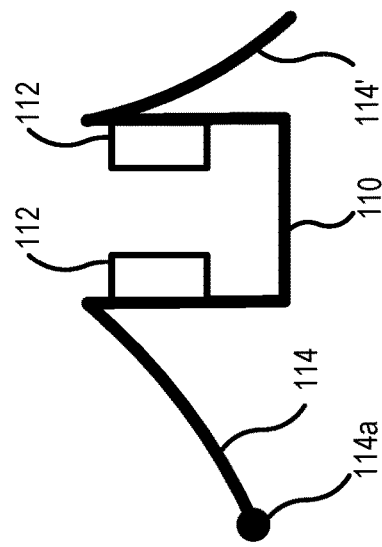
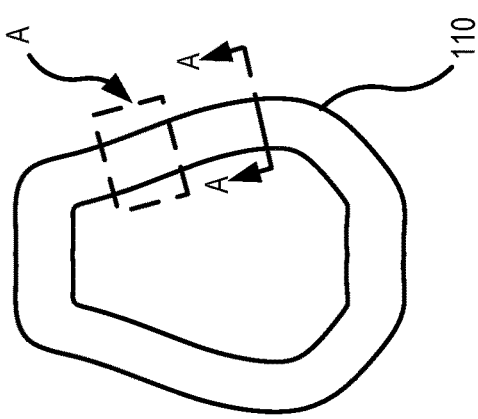
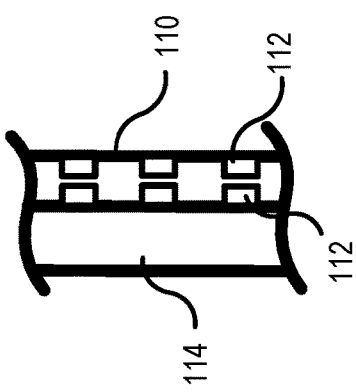
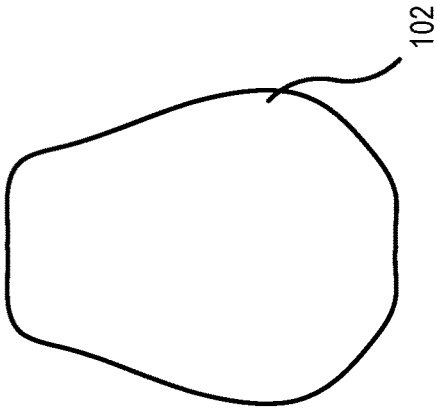
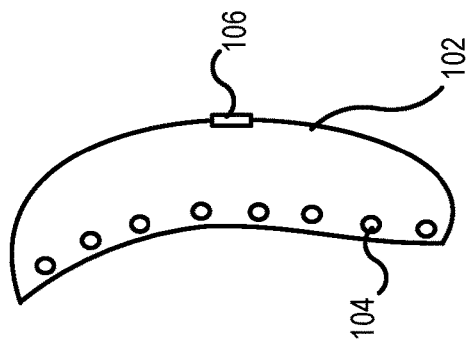

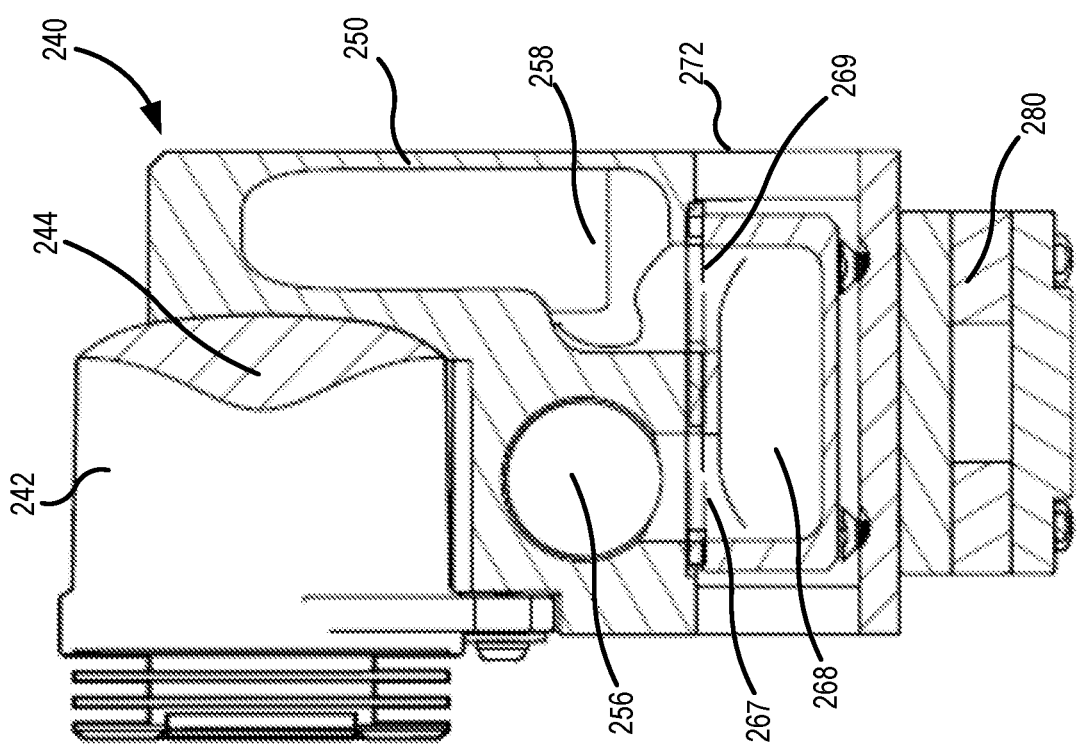
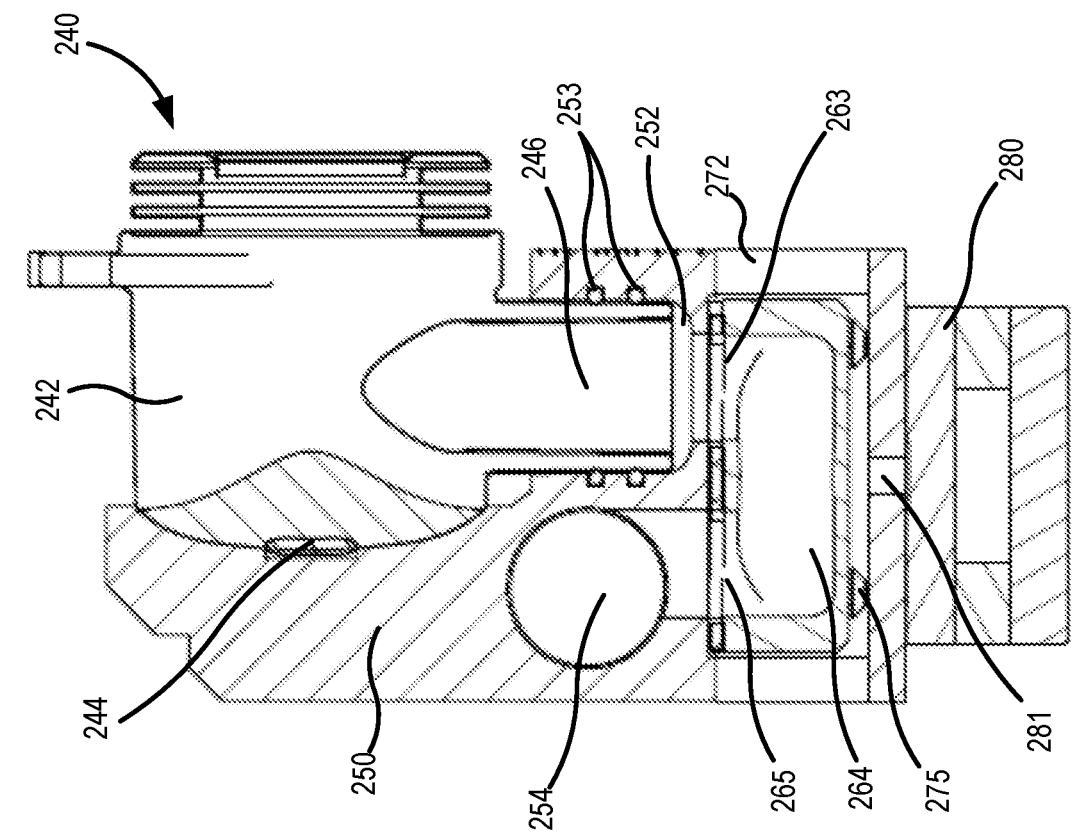

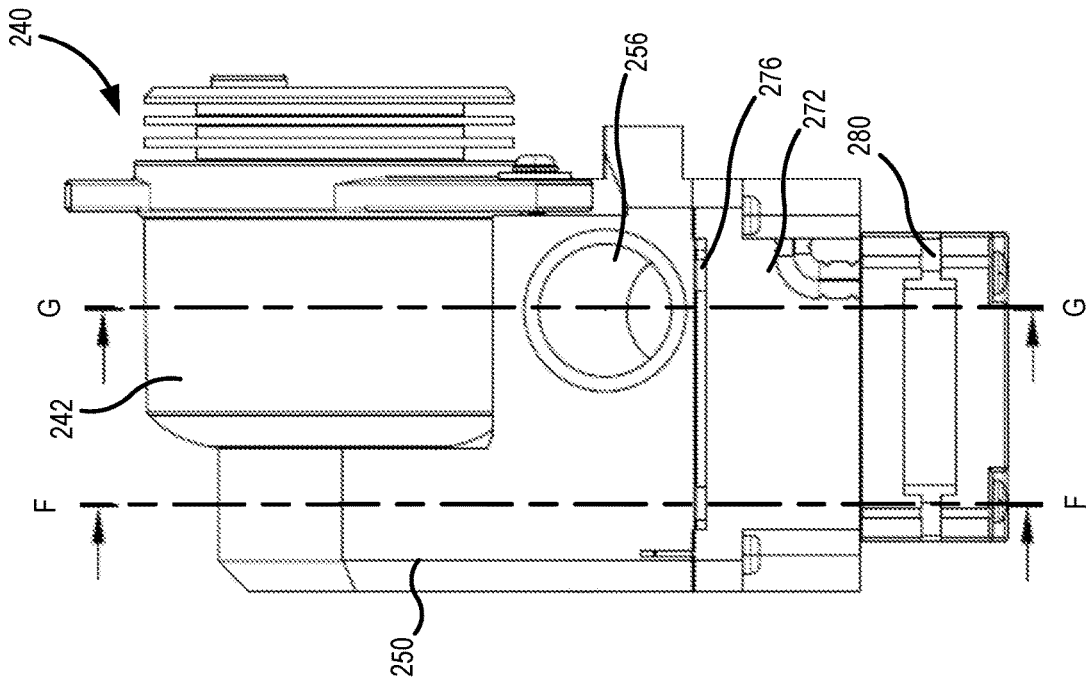
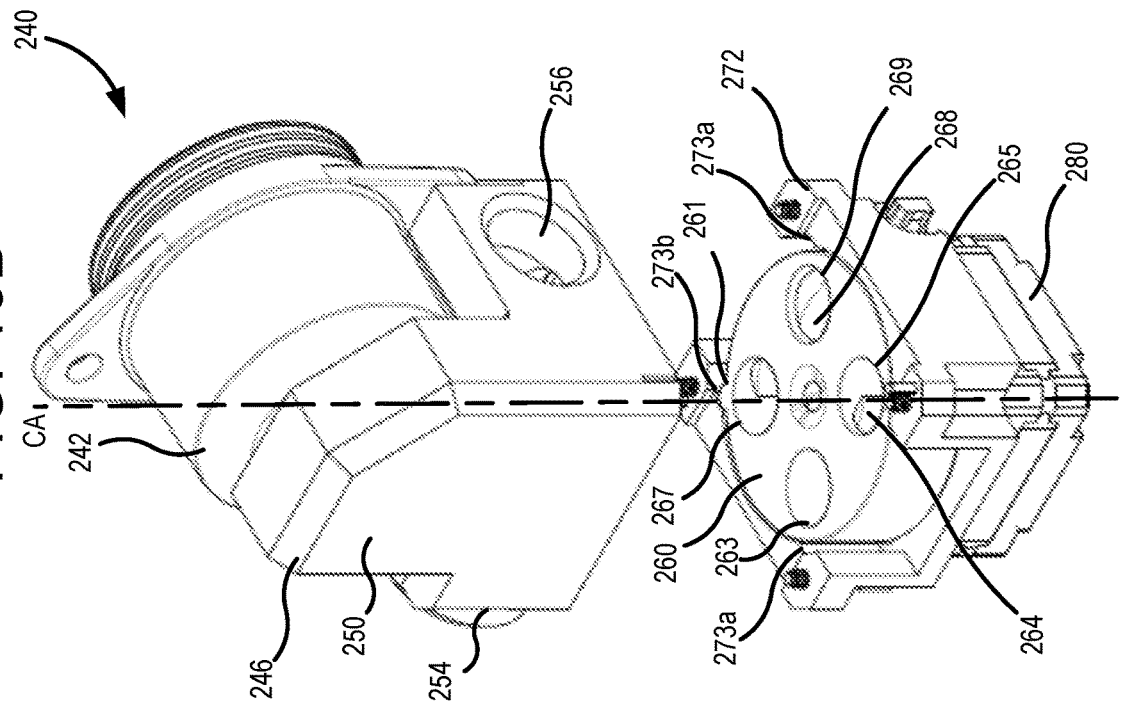

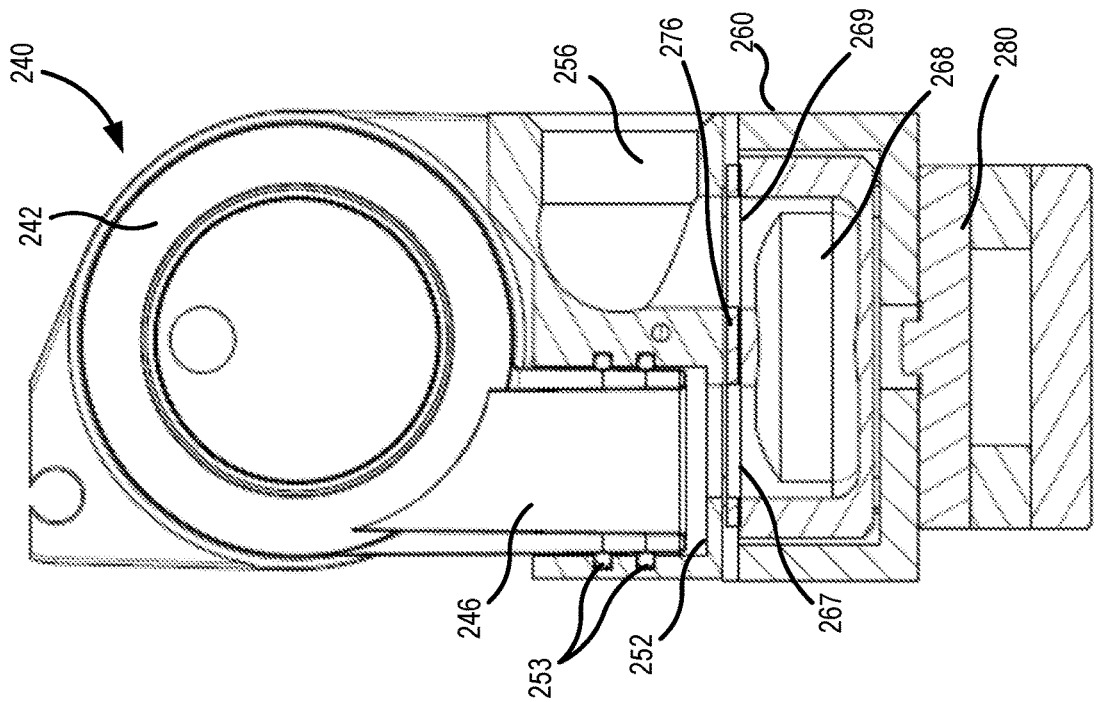
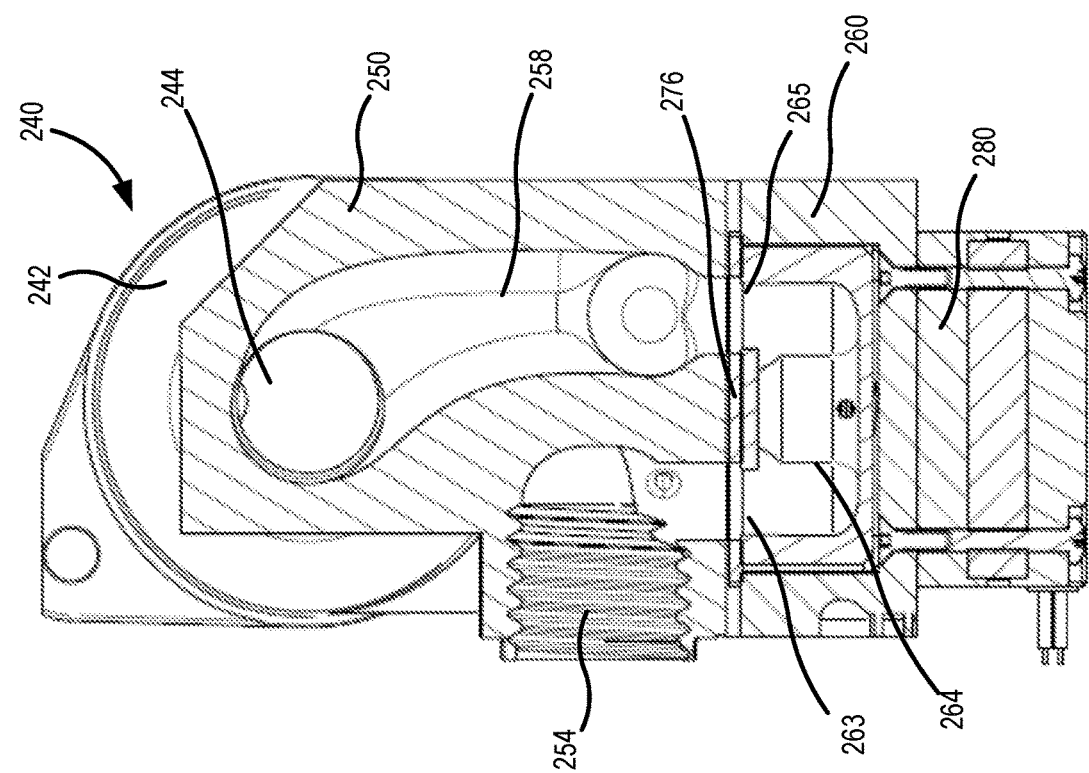

US 11,839,587 B1

SYSTEMS, DEVICES, AND METHODS FOR AMBULATORY RESPIRATION ASSISTANCE

STATEMENT CONCERNING GOVERNMENT SUPPORT

This invention was made with government support under Grant No. 1R43HL146732-01 awarded by the National Institutes of Health. The government has certain rights in the invention.

TECHNICAL FIELD

The present disclosure relates generally to systems, devices, and methods for providing respiration assistance, and more particularly, to external positive/negative pressure ventilators for providing respiratory assistance to users suffering from dyspnea on exertion (DOE) due to respiratory disorders such as chronic obstructive pulmonary disease (COPD) and/or the like.

BACKGROUND

COPD is an obstructive lung disease that affects 15 million Americans each year. Of these, approximately twenty percent suffer from severe DOE that drastically limits their daily activities. COPD patients experience DOE for a variety of reasons, with smoking as the primary cause. Most cases of COPD can be prevented by reducing exposure to risk factors, and while the disease remains one that may be treated, no cure is currently known. To combat DOE in COPD and other respiratory disorders, support and/or assistance tends to be helping the patient breathe out faster in order to prevent dynamic hyperinflation and to offload the work of the respiratory muscles.

Historically, COPD has been treated with supplemental oxygen, various therapeutics such as bronchodilators or corticosteroids, and/or various surgical procedures. In addition, external negative pressure ventilators (NPV) and/or mechanical respirators have been used to assist breathing when muscle control is lost and/or when the work of breathing exceeds a patient's ability. For example, "iron lungs" have been used to assist the breathing of users suffering with polio or other pathologies effecting respiration. Iron lungs, however, are large, immobile devices that confine and restrict the user. Attempts to reduce the size of external NPVs and/or mechanical respirators have allowed for a degree of portability, but challenges persist. For example, known devices tend to include a shell or "cuirass" that is worn by a user and connected to a relatively large ventilator via a hose or the like. While such devices may have a degree of portability, they generally do not allow for ambulatory use (e.g., do not allow the user to move or walk freely without being tethered to a relatively large and/or cumbersome ventilator). In certain instances, cuirass or other wearable devices that assist in clearing mucous from the user's air pathways have proven to be somewhat effective. However, none of these treatment or assistance options provide a universal and/or ambulatory approach for all patients, and thus those with COPD and/or other respiratory deficiencies continue to suffer despite treatment or assistance. Accordingly, a need exists for improved systems, devices, and/or methods for ambulatory respiration assistance.

SUMMARY

Embodiments described herein relate to systems, methods, and devices for respiration assistance such as external positive/negative pressure ventilators for providing respiratory assistance to users suffering from DOE due to respiratory disorders like COPD, etc. In particular, systems, methods, and devices described herein relate to respiration assistance systems that includes a cuirass configured to be disposed on at least a portion of a thorax of a user, and a ventilator that is fluidically coupled to the cuirass. The ventilator can include at least a pump, a valve and an actuator coupled to the valve. The valve is configured to be in a first configuration during exhalation of the user (e.g., a patient, a person on whom the device is being tested, etc.) in which (i) a first flow path defined by the valve fluidically couples an outlet of the pump to a volume defined by the cuirass and (ii) a second flow path defined by the valve fluidically couples an inlet of the pump to an external environment, and in a second configuration during inhalation of the user such that the first flow path fluidically couples the inlet of the pump to the cuirass and the second flow path fluidically couples the outlet of the pump to the external environment.

In some embodiments, a system includes a cuirass configured to be coupled to at least a portion of a thorax of a user such that a first internal volume is defined between a surface of the cuirass and at least the portion of the thorax. A ventilator is fluidically coupled to the cuirass so as to be in fluidic communication with the first internal volume. The ventilator includes a housing defining a second internal volume and at least one opening to allow air to flow into or out of the housing. A pump is disposed within the second internal volume, the pump including an inlet and an outlet. A valve is disposed in the second internal volume, the valve defining a first flow path and a second flow path. An actuator is operatively coupled to the valve, and a controller is in communication with the actuator. In response to determining that the user is exhaling, the controller is configured to cause the actuator to move the valve into a first configuration in which the first flow path fluidically couples the outlet to the first internal volume and the second flow path fluidically couples the inlet to the second internal volume. In response to determining that the user is inhaling, the controller is configured to cause the actuator to move the valve into a second configuration in which the first flow path fluidically couples the inlet to the first internal volume and the second flow path fluidically couples the outlet to the second internal volume.

In some embodiments, an apparatus includes a pump including an inlet and an outlet. A manifold is coupled to the pump. The manifold defines a first channel fluidically coupled to the outlet, a second channel configured to be fluidically coupled to an interior volume of a cuirass, a third channel fluidically coupled to a volume external to the manifold, and a fourth channel fluidically coupled the inlet. The apparatus also includes a valve that defines a first flow path and a second flow path. When the valve is in a first configuration, the first flow path fluidically couples the first channel to the second channel and the second flow path fluidically couples the third channel to the fourth channel. When the valve is in a second configuration, the first flow path fluidically couples the second channel to the fourth channel and the second flow path fluidically couples the first channel to the third channel.

In some embodiments, a valve assembly for a respiration assistance system having a pump and a cuirass includes a valve defining a first flow path and a second flow path. An actuator is coupled to the valve and is configured to rotate the valve about a central axis between a first angular orientation and a second angular orientation. When the valve is in the first angular orientation, the first flow path fluidically couples an outlet of the pump to an inlet of the cuirass and the second flow path fluidically couples an inlet of the pump to an external environment. When the valve is in the second angular orientation, the first flow path fluidically couples the inlet of the pump to the inlet of the cuirass and the second flow path fluidically couples the outlet of the pump to the external environment.

In some embodiments, a respiration assistance system includes a pump having an inlet and an outlet, a valve defining a first flow path and a second flow path, an actuator coupled to the valve, a controller, and a sensor, and a cuirass configured to be coupled to at least a portion of a thorax of a user such that a volume is defined between an internal surface of the cuirass and at least the portion of the thorax. In some implementations, a method for controlling the respiration assistance system includes receiving, at the controller and from the sensor, a first signal associated with the user exhaling. The controller actuates the actuator to move the valve into a first angular orientation in which the first flow path fluidically couples the outlet to the volume and the second flow path fluidically couples the inlet to an external environment, and the pump communicates air from the external environment into the volume. The method also includes receiving, at the controller and from the sensor, a second signal associated with the user inhaling. The controller actuates the actuator to move the valve into a second angular orientation in which the first flow path fluidically couples the inlet to the volume and the second flow path fluidically couples the outlet to the external environment, and communicating, via the pump, air from the volume to the external environment.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 2A is front view and FIG. 2B is a side view of the cuirass included in the system of FIG. 1.

FIG. 2C is a front view of a sealing member coupled to the cuirass of the system of FIG. 1; FIG. 2D is front view of a portion of the sealing member indicated by the region A in FIG. 2C; FIG. 2E is a side cross-section view of the sealing member taken along the line A-A in FIG. 2C.

FIG. 2F is a side cross-section view of the sealing member, as shown in FIG. 2E, including one or more optional features and/or components.

FIGS. 17C and 17D are rear cross-section views of the pumping assembly of FIG. 17B taken along the lines D-D and E-E in FIG. 17B, respectively.

FIG. 18B is a partial exploded front perspective view of the pumping assembly with the valve in the second angular orientation; FIG. 18C is a rear view of the pumping assembly of FIG. 18B in an assembled configuration; and FIGS. 18D and 18E are side cross-section views of the pumping assembly of FIG. 18C taken along the lines F-F and G-G in FIG. 18C, respectively.

Figure 1:
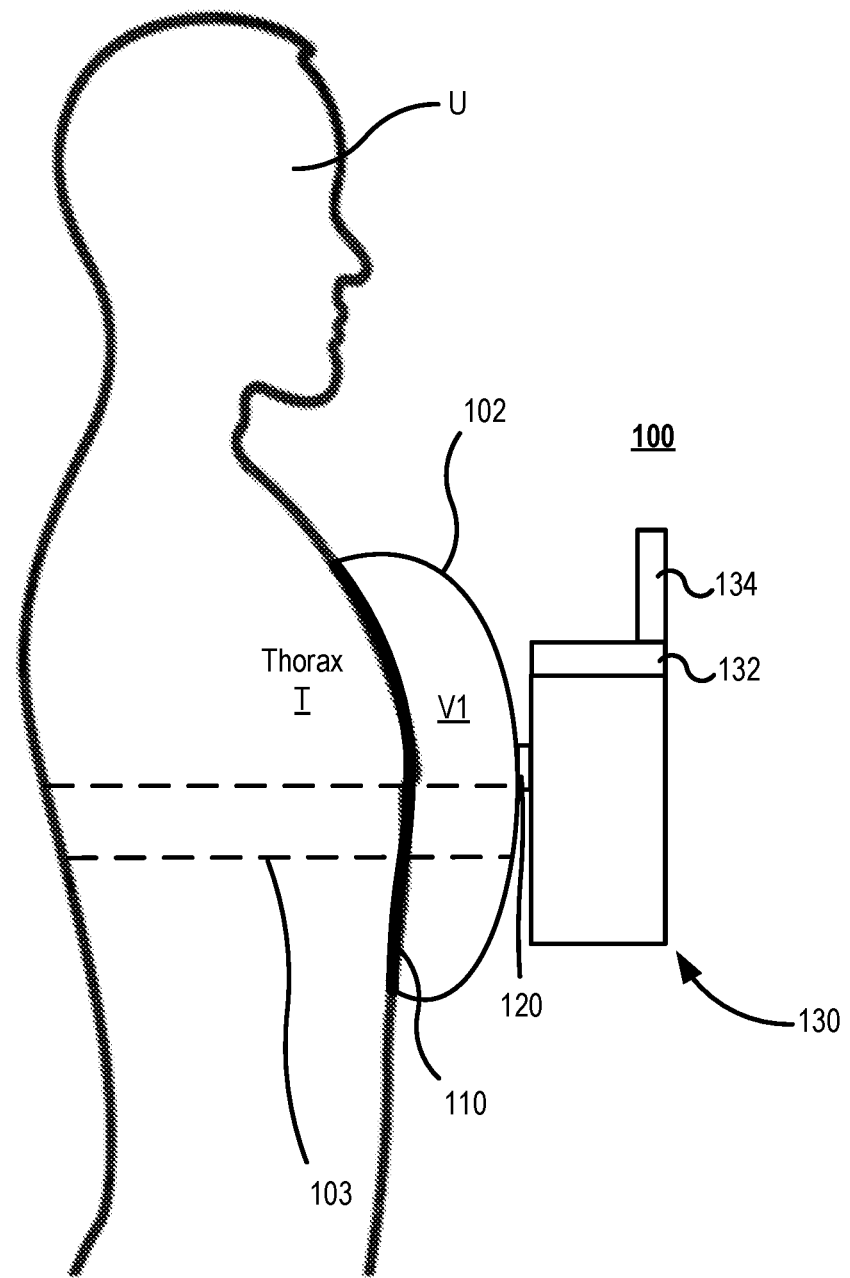
FIG. 1 is a schematic illustration of a respiration assistance system that includes a cuirass and a ventilator coupled to the cuirass, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Systems, devices, and methods described herein are configured to assist with respiration in patients that suffer from COPD or other respiratory disorders which hinders such patients from breathing on their own. Systems, devices, and methods described herein reduce muscular effort and energy required by a patient during inhalation and exhalation, for example, by selectively providing positive pressure, negative pressure, or a combination thereof in an internal volume of a cuirass that is worn on at least a portion of a thorax of the patient, for example, on a chest and/or abdomen of the patient. The pressure assists the patient in breathing by either pushing in or pulling out the chest of the patient. A positive pressure within the interior volume of the cuirass pushes or compresses the chest of the patient inward to assist in exhalation and a negative pressure within the interior volume creates a suction force on or a decompression of the chest of the patient to assist in inhalation. Systems, devices, and methods described herein may also include one or more sensors to selectively apply positive or negative pressure within the internal volume of the cuirass to match the patient's breathing cycle or pattern, this increasing efficiency, effectiveness, and comfort.

Conventional respiration assistance systems are plagued with various problems that make it difficult for patients needing respiration assistance to adopt such conventional systems. For example, conventional respiration assistance systems can be bulky and heavy such that at least portions of such conventional systems, for example, machinery used to provide positive and negative pressure on the chest and/or abdomen of the patient, cannot be worn on the patient's person. For example, such machinery may have to be mounted on wheels or a some form a movable trolley that the patient pulls along therewith. Such conventional systems interfere with the mobility of the patient thereby, decreasing patient comfort and convenience. Another issue with conventional respiration assistance systems is reliability and life. Conventional respiration assistance systems can include multiple valves and other moving parts. An average person breathes about 17,000 to about 23,000 times per day (including inhaling and exhaling). This can amount to more than about 6 million to about 8 million breathing cycles per year. Multiple valves and other moving parts of such conventional systems can fail may not be able to withstand such large number of cycles and are therefore, prone to failure which decreases reliability and increases maintenance costs. Moreover, the presence of multiple moving parts can increase the complexity of such conventional systems that can decrease reliability, and increase manufacturing as well as maintenance costs.

Embodiments of the systems, apparatus, and methods described herein for providing respiration assistance to a user may provide one or more benefits including but not limited to, for example: (1) having a light weight and compact design such that a cuirass as well as a ventilator of the system can be worn on at least a portion of a thorax of a user, thereby increasing user mobility and increasing user comfort and convenience; (2) disposing a ventilator of the system in front of the user when the system is worn by the user such that the user can easily engage with and operate the ventilator, for example, through an interactive display of the ventilator; (3) providing a single valve that can selectively and reliably move to cause air to be communicated into an internal volume of the cuirass when the user exhales, and cause air to drawn out of the internal volume when the user inhales, thus reducing moving parts and increasing reliability; (4) providing a compact valve design that allows rapid switching of the valve to provide inhalation or exhalation support to the user, thus reducing breathing support delays and increasing user comfort; (5) limiting motion and increasing reliability of the valve such that the valve can be operated for millions of cycles without any significant degradation in performance of the valve, thus increasing reliability and reducing maintenance costs; and (6) providing flow paths through the valve and, optionally, a manifold that allow the pump to be continuously operated in a single flow direction during inhalation or exhalation being performed by the user, thereby obviating stopping and starting of the pump, which increases pump life and reduces maintenance costs.

The term "thorax" as described herein refers to the region between the abdomen inferiorly and the root of the neck superiorly of a user. The terms "chest" or "abdomen" as used herein is meant to encompass the anterior portion of a human's chest or abdomen. The addition of the phrase "the anterior portion" as used herein is meant as clarification rather than to refer to a distinct portion of the chest or abdomen of the patient. The term "torso" as used herein refers to the portion of a human's body that includes the chest, abdomen, and back and may be used to refer to any area within that portion of the body.

The term "internal volume" as used herein with respect to the cuirass is meant to encompass and/or refer to the approximate volume of the space defined by the interior face of the cuirass and the surface of the body of the user wearing the cuirass that is encircled by the border of the cuirass. If a patient is not wearing the cuirass, the interior volume may be approximated as the space defined by the interior face of the cuirass and a roughly flat plane projected across the border of the cuirass. In certain contexts, the internal volume of the cuirass may be referred to herein and in the appended claims as a "first internal volume."

The term "internal volume" as used herein with respect to the ventilator is meant to encompass and/or refer to the approximate inner volume of a housing that is included in the ventilator and within which at least some of the components of the ventilator are disposed. In certain contexts, the internal volume of the ventilator may be referred to herein and in the appended claims as a "second internal volume."

The term "interior face" as used herein with respect to the cuirass is meant to encompass and/or refer to the side of the cuirass that, when the cuirass is worn by a patient, is facing towards the torso of the patient. The term "exterior face" as used herein is meant to encompass and/or refer to the side of the shell that, when the cuirass is worn by a patient, is facing away from the torso of the patient.

The term "negative pressure" as used herein is meant to encompass and/or refer to a pressure within the interior volume of a cuirass below the ambient pressure, or in other words, a suction force being applied to the internal volume of the cuirass.

The term "positive pressure" as used herein is meant to encompass and/or refer to a pressure within the interior volume of a cuirass above the ambient pressure, that is air being communicated under pressure into the internal volume.

The term "cuirass" as used herein is meant to encompass and/or refer to a generally shell-shaped structure that fits over at least a portion of the thorax of the user (e.g., an anterior chest and/or the anterior abdomen), with the space between the thorax and the shell of the cuirass configured to be alternately pressurized and evacuated by a ventilator.

The term "example" as used herein to describe various embodiments, arrangements, and/or implementations is intended to indicate that such embodiments, arrangements, and/or implementations are possible examples, representations, and/or illustrations of possible embodiments, arrangements, and/or implementations (and such term is not intended to connote that such embodiments, arrangements, and/or implementations are necessarily required, crucial, extraordinary, or superlative examples).

The terms "including," "comprising," "having," "containing," or "involving" and variations thereof as used herein, are meant to encompass and/or refer to the items listed thereafter as well as, optionally, additional items. In the description the same numerical references refer to similar elements.

As used in this specification and the appended claims, the singular form "a," "an," and "the" include plural referents unless the context clearly dictates otherwise.

As used herein, the terms "about" or "generally" and/or the like in the context of a given value or range (whether direct or indirect, e.g., "generally in line," "generally aligned," "generally parallel," etc.) refers to a value or range that is within 20%, preferably within 10%, and more preferably within 5% of the given value or range.

As used herein, the term "and/or" is to be taken as specific disclosure of each of the two 10 specified features or components with or without the other. For example, "A and/or B" is to be taken as specific disclosure of each of (i) A, (ii) B and (iii) A and B, just as if each is set out individually herein.

In the context of the present specification, the words "first," "second," "third," etc. have been used as adjectives only for the purpose of allowing for distinction between the nouns that they modify from one another, and not for the purpose of describing any particular relationship between those nouns. Thus, for example, it should be understood that the use of the terms "first portion" and "second portion" is not intended to imply any particular type, hierarchy, necessary ordering or ranking (for example) of/between the units unless expressly stated otherwise. Nor is their use (by itself) intended to imply that any "second unit" must necessarily exist in any given situation.

As utilized herein, the terms "substantially" and similar terms are intended to have a broad meaning in harmony with the common and accepted usage by those of ordinary skill in the art to which the subject matter of this disclosure pertains. For example, the term "substantially flat" would mean that there may be de minimis amount of surface variations or undulations present due to manufacturing variations present on an otherwise flat surface. It should be understood by those of skill in the art who review this disclosure that these terms are intended to allow a description of certain features described and claimed without restricting the scope of these features to the precise arrangements and/or numerical ranges provided. Accordingly, these terms should be interpreted as indicating that insubstantial or inconsequential modifications or alterations of the subject matter described and claimed are considered to be within the scope of the inventions as recited in the appended claims.

The terms "coupled," and the like as used herein mean the joining of two members directly or indirectly to one another. Such joining may be stationary (e.g., fixed, permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

Referring to the figures, FIG. 1 is a schematic illustration of a respiration assistance system 100 that includes a cuirass 102 and a ventilator 130 having a power supply 132 and a display 134, coupled to the cuirass 102, according to an embodiment. The cuirass 102 is configured to be coupled to at least a portion of a thorax T of a user U such as a patient, a person on who the system 100 is being tested, etc., (e.g., on the chest, on a portion of a chest, on an abdomen, on a portion of the abdomen, or a portion of a chest and a portion of the abdomen of the user U) such that a first internal volume V1 is defined between a surface of the cuirass 102 and at least a portion of the thorax T. A sealing member 110 is coupled along a peripheral edge of the cuirass 102 and configured to be disposed between the peripheral edge of the cuirass 102 and at least the portion of the thorax T when the cuirass 102 is coupled thereto such that the sealing member 110 forms a fluid tight seal with at least the portion of the thorax T or a fabric disposed on at least the portion of the thorax T (e.g., a vest, shirt, blouse, or another piece of fabric being worn by the user U). The cuirass 102 may be secured to the user by a securement 130.

Expanding further, FIG. 2A is a front view and FIG. 2B is a side view of the cuirass 102 included in the system 100. The cuirass 102 has a shape or profile that may correspond to or resemble the portion of the thorax T of the user U on which the cuirass 102 is disposed and coupled to. The cuirass 102 may be formed from a rigid or semi-rigid material (e.g., plastics, polycarbonate, polymers, any other suitable material or a combination thereof) having the sealing member 110 coupled along a peripheral edge thereof that is shaped for engagement with at least the portion of the thorax T (e.g., anterior chest and/or abdomen of the user U). The cuirass 102 has a concave inner surface or face shaped so that when the sealing member 110 is engaged with the thorax T of the user U, a first internal volume V1 is formed between the inner surface of the cuirass 102 and the corresponding portion of the thorax T. The first internal volume V1 (e.g., an inflatable volume) is configured to receive air from the ventilator 130.

A compressive force is exerted on the portion of the thorax T of the user U when air is filled into the first internal volume V1 to assist the user in exhaling air, and a pulling force is exerted on the portion of the thorax T when air is evacuated from the first internal volume V1 to assist the user U in inhaling air. In some embodiments, the cuirass 102 may be custom made to correspond to a shape of the portion of the thorax T of the user U. For example, a three dimensional (3D) scan of the thorax T or portion of the thorax T of the user U may be obtained and the cuirass 102 may be custom molded or 3D printed based on the 3D scan of the thorax T of the user U. In some embodiments, the peripheral edge of the thorax T may be shaped to match or mimic the curvature of the thorax T of the user U. By having the peripheral edge closely match the curvature of the patient's thorax T, the peripheral edge of the cuirass 102 and thereby the sealing member 110 coupled thereto can fully engage the thorax T, which reduces leakage of air from or to the first interior volume. In some embodiments, instead of using 3D scanning, the peripheral edge can be an approximate of the curves of the thorax T of the user U.

In some embodiments, the cuirass 102 may be made of a transparent or semi-transparent material. The transparent or semi-transparent cuirass 102 may provide the benefit of allowing optical sensors that are not mounted within the cuirass 102 to obtain measurements within the first interior volume (e.g., temperature measurements, pressure measurements, etc.). Moreover, having a transparent cuirass 102 may allow a caregiver such as a doctor to observe the thorax T of the user U while the user U is wearing the system 100. In some embodiments, the cuirass 102 may be made of an opaque material. In some embodiments, the cuirass 102 may be made of an opaque material and include transparent or semi-transparent portions (e.g., windows). In some embodiments, the cuirass 102 may include one or more ribs protruding from the exterior face of the cuirass 102. In some embodiments, the ribs may be solid such that the interior face of the cuirass 102 is approximately flat between the portion of the interior face opposite the rib and the portion of the interior face opposite the exterior face without a rib adjacent to the rib. In some embodiments, the ribs may be hollow, such that the interior face opposite the rib defines an outward curvature corresponding to the curvature of the ribs. Solid ribs may provide structural strength to the cuirass, while hollow ribs may allow for additional components to be mounted within the first interior volume. In some embodiments, the cuirass 102 may include at least one plate that may be formed of a rigid material (e.g., hard plastics or metals), for example, for providing structural support and strength to the cuirass 102. Various examples of the cuirasses 102 that may be included in the system 100 are described in U.S. patent application Ser. No. 17/413,740 (the '740 application), filed Jun. 14, 2021, and entitled "Improvements on Ambulatory Respiratory Assist Device," the entire disclosure of which is incorporated herein by reference.

The cuirass 102 is coupled to the thorax T via the securement 103 so as maintain the sealing member 110 in sealing relationship with the portion of the thorax T or a fabric disposed on the portion of the thorax T, as well as to support the weight of the cuirass 102 and the ventilator 130, particularly when the patient is standing in an upright position. The securement 103 may include one or more band, belt, chain, or straps that may be secured around a portion of the thorax T or another portion of the body of the user U via clips, couplers, Velcro, buckles, latches, etc. In some embodiments, the one or more securements 103 may be configured to be disposed around a region of the waist and/or chest of the user U. In some embodiments, the securement 103 may be configured to be secured around a region of the pelvic girdle of the user U, and/or the inferior border of sternum of the user U. All such securements are contemplated and should be considered to be within the scope of the present disclosure. In some embodiments, the securement 103 may include a first belt configured to be disposed around a waist or abdomen of the user U, and a second belt connected to the cuirass 102 at two locations remote from the first belt and adapted to extend around the back of the user U from one of the two locations to the other. In some embodiments, the securement 103 may include a vest or other garment adapted to be worn by the user U, with the cuirass 102 being fixedly or removably attached to the vest or other garment. Various examples of securements 103 that may be included in the system 100 are described in the '740 application, as well as U.S. patent application Ser. No. 16/086,892 (the '892 application), filed Sep. 20, 2018, and entitled "Ambulatory Respiratory Assist Device," the entire disclosure of which is incorporated herein by reference.

FIGS. 2C-2F show various views of the sealing member 110 that may be coupled to peripheral edge of the cuirass 102 and configured to be disposed between the peripheral edge of the cuirass 102 and at least the portion of the thorax T when the cuirass 102 is coupled thereto such that the sealing member 110 forms a fluid tight seal or a substantial fluid tight seal with at least the portion of the thorax T or a fabric disposed on at least the portion of the thorax T. The sealing member 110 may be formed from a soft and flexible material, for example, rubber, silicone, polyurethane, resilient and compressible foam.

In some embodiments, the sealing member 110 may be over molded over the peripheral edge of the cuirass 102. In such embodiments, the cuirass 102 may define multiple indents or through-holes 104 proximate to the peripheral edge of the cuirass 102 (FIG. 2B). As shown in FIGS. 2D and 2E, over molding of the sealing member 110 over the peripheral edge of the cuirass 102 can cause protrusions 112 to protrude from an inner surface or coupling region of the sealing member 110 that faces the peripheral edge of the cuirass 102 to protrude or enter into or through corresponding indents or through-holes 104 defined in the cuirass 102, thus securing the sealing member 110 to the cuirass 102. In some embodiments, the sealing member 110 may be separately molded such that the sealing member 110 includes the protrusions 112 located on an interior surface thereof which correspond to the locations of the indents or through-holes 104 formed proximate to the peripheral edge of the cuirass 102. In such embodiments, the sealing member 110 may be snap-fit, press-fit, etc. over the peripheral edge of the cuirass 102 by inserting the protrusions 112 into the corresponding indents or through-holes 104. In this manner, the sealing member 110 may be removed and replaced easily with a new sealing member once the sealing member 110 has been worn for a sufficiently long period of time or is near its end of life. In some embodiments, the sealing member 110 may be coupled to the cuirass 102 using coupling members (e.g., fasteners such as screws, nuts, bolts, rivets, clips, clamps, etc.). In some embodiments, the sealing member 110 may be friction fit to the peripheral edge of the cuirass 102. In some embodiments, the sealing member 110 may be fixedly coupled to the peripheral edge of the cuirass (e.g., via adhesives, fusion bonding, thermal bonding, etc.).

The sealing member 110 may include any suitable features to enable the sealing member 110 to form a substantially fluid tight seal with the thorax T of the user U (e.g., at least a portion of the chest and/or abdomen of the user U), or a fabric (e.g., vest or shirt) disposed over the thorax T. In some embodiments, the sealing member 110 may include a solid structure that is formed from a relatively soft and flexible material that can flex, compress, or comply as it is pressed against the thorax T of the user U (e.g., via the securement 103 urging the cuirass 102 towards the thorax T of the user U) to form a substantially fluid tight seal therewith. In some embodiments, the sealing member 110 may have a hollow core such that when the sealing member 110 is pressed against the thorax T, it spreads laterally outwards to cause a larger surface of the sealing member 110 to press against the thorax T and form a substantially fluid tight seal therewith.

In some embodiments, the sealing member 110 may form a skirt or flap extending from at least one side of the peripheral edge of the cuirass 102. For example, FIG. 2E is a side cross-section view of the sealing member taken along the line A-A in FIG. 2C. As shown in FIG. 2E, the sealing member 110 includes a skirt 114 extending from an inner edge of the sealing member 110 located proximate to the peripheral edge of the cuirass 102 and within the first internal volume V1. As described before, the sealing member 110 is formed of a relatively soft and flexible material, which allows the skirt 114 to form the substantial fluid tight seal with at least the portion of the thorax T or the fabric disposed on at least the portion of the thorax T while the user U is inhaling and while the user U is exhaling (e.g., when exposed to positive pressure and/or negative pressure).

In some embodiments, the sealing member 110 can include one or more additional and/or optional features configured to facilitate the formation of a fluid tight seal. For example, FIG. 2F shows the sealing member 110 including the skirt 114 (e.g., a first skirt) extending inwardly from an inner or first edge of the sealing member 110 that is located on or proximate to an inner surface of the cuirass 102 such that the first skirt 114 is inside the first internal volume V1, and further including an additional skirt 114' (e.g., a second skirt) extending from an outer or second edge of the sealing member 110 that is located on an outer surface of cuirass 102 proximate to the outer peripheral edge thereof such that the second skirt 114' is located outside the first internal volume V1. The second skirt 114 may be configured to form a second fluid tight seal with at least the portion of the thorax T or the fabric disposed on at least the portion of the thorax T while the user U is inhaling and while the user U is exhaling, thus providing additional sealing and redundancy Said another way, the sealing member 110 may be a double-skirted or double-lipped seal with the first skirt 114 (or first lip) being located on the side of the sealing member 110 facing the first internal volume V1 of the cuirass 102 and the second skirt 114' (or second lip) being located on the opposite side of the sealing member 110. In some implementations, such a double-skirted (or double-lipped) sealing member 110 may inhibit leakage by engaging one of the first skirt 114 or the second skirt 114' when positive pressure is exerted, and the other of the first skirt 114 or the second skirt 114' when negative pressure is exerted. For example, when negative pressure is exerted, the sealing member 110 may be pulled inwards towards the first internal volume V1 and the second skirt 114' may be engaged. When positive pressure is exerted, the sealing member 110 may be pushed outwards away from the first internal volume V1 and the first skirt 114 may be engaged. In some embodiments, each of the first skirt 114 and the second skirt 114' may be engaged during each of a positive pressure or a negative pressure being applied within the first internal volume V1. The first skirt 114 and the second skirt 114' may be substantially the same size, shape, and/or configuration or may be different sizes, shapes, and/or configurations. For example, FIG. 2F shows the second skirt 114' having a substantially similar configuration as the first skirt 114, but having a smaller size. In other embodiments, any suitable combinations of sizes, shapes, and/or configurations of the skirts 114 and 114' may be used to achieve the desired fluid tight sealing characteristics. In some embodiments, the sealing member 110 may include any sealing member described in the '892 application that is incorporated herein by reference.

FIG. 2F also illustrates the seal member 110 and/or the skirt 114 including an optional feature along an internal edge of the skirt 114. For example, in some embodiments, it may be desirable to form a protrusion, bead, rib, fork, flare, and/or any other suitable edge feature (collectively referred to herein as "edge feature 114a") that may facilitate the formation of a fluid tight seal. The inclusion of the edge feature 114a can limit and/or reduce a likelihood of the skirt 114 becoming inverted, bent, folded, and/or otherwise reconfigured in response to positive pressure and/or negative pressure. In some embodiments, the edge feature 114a can be a protrusion, bead, rib, etc. formed by embedding a wire, filament, string, etc. within the edge portion of the skirt 114. In some embodiments, the edge portion of the skirt 114 can be molded over such a wire, filament, string, etc., thereby forming the protrusion, bead, rib, and/or the like. In other embodiments, the edge feature 114a can be and/or can have any other suitable configuration. For example, the skirt 114 can be arranged to gradually increase in thickness along a width of the skirt 114 moving outwardly toward the edge portion. In still other embodiments, the edge feature 114a and/or any other suitable portion of the skirt 114 can have any suitable configuration that can facilitate the formation of the desired sealing characteristics.

The cuirass 102 can also define an aperture 106 therethrough, for example, on a portion of the cuirass 102 that faces the ventilator 130. The cuirass 102 can be fluidically and, optionally, physically coupled to the ventilator 130 via the aperture 106. In some embodiments, the system 100 may also include a flow member 120 that is at least partially disposed through the aperture 106 and/or fluidically coupled to the aperture 106, the flow member 120 being fluidically and, optionally physically coupled to the ventilator 130 so as to couple the ventilator 130 (e.g., fluidically and, optionally, physically couple) to the first internal volume V1 of the cuirass 102. In some embodiments, at least a portion of the flow member 120 may be disposed through the aperture 106. In some embodiments, the flow member 120 may include a first portion having a first end coupled to the ventilator 130 (e.g., a manifold 150 included in the ventilator 130 as described with respect to FIG. 3) and a second end disposed through the aperture 106.

The flow member 120 may also include a second portion disposed on an inner surface of the cuirass 102 within the first internal volume V1. The second portion may have a cross-sectional width that is larger than a cross-sectional width (e.g., diameter) of the aperture 106 such that once the first portion is coupled to the ventilator 130, a wall of the cuirass 102 is secured or clamped between the second portion and the ventilator (e.g., a corresponding wall of a housing 131 of the ventilator 130 shown in FIG. 3), thereby securing the cuirass 102 to ventilator 130. In some embodiments, a gasket or any other sealing member may be disposed between the inner surface of the cuirass 102 and a corresponding surface of the second portion so as to fluidically seal the first internal volume V1 from an external environment located outside the first internal volume V1.

In some embodiments, the flow member 120 may define one or more axial flow channels from the first portion to the second portion, the one or more axial flow channels fluidically coupling the ventilator to the first internal volume V1. In some embodiments, multiple slots may be defined at a proximate end of the one or more axial flow channels, which is located within the first internal volume V1, and/or a distal end of the one or more axial flow channels located on a distal end of the first portion located proximate to the ventilator 130. The multiple slots may serve as diffusers to diffuse the flow of air entering or exiting the first internal volume V1 to facilitate uniform distribution of the air into the first internal volume V1, and may also serve to suppress a noise level of the air traveling to or from the internal volume so as to increase user comfort. In some embodiments, the second portion of the flow member 120 may also define one or more second flow channels separate from the one or more axial flow channels. The second flow channels may provide additional flow paths for fluidically coupling the first internal volume V1 to the one or more axial flow channels. For example, the one or more axial flow channels may be oriented along a first axis that runs along a longitudinal axis of the first portion, and the one or more second flow channels may be oriented along a second axis that is angularly offset from the first axis (e.g., oriented at an angle in a range of 70 degrees to about 110 degrees, inclusive (e.g., at an angle of about 90 degrees) with respect to the first axis. One or more openings may be defined in a wall of the one or more axial channels to fluidically couple the one or more second channels to the one or more first channels. The one or more second flow channels may provide an alternate flow path to spread the air as it is communicated from the ventilator 130 to the first internal volume V1, for example, to allow rapid, controlled, and/or uniform filling of the first internal volume V1 with air during exhalation by the user U. The one or more second flow channels may also lower resistance for air to be drawn out of the first internal volume V1, as well as more uniformly draw the air out of the first internal volume V1 so as to allow a more uniform suction force to be exerted on the thorax T during inhalation by the user U.

Figure 3:
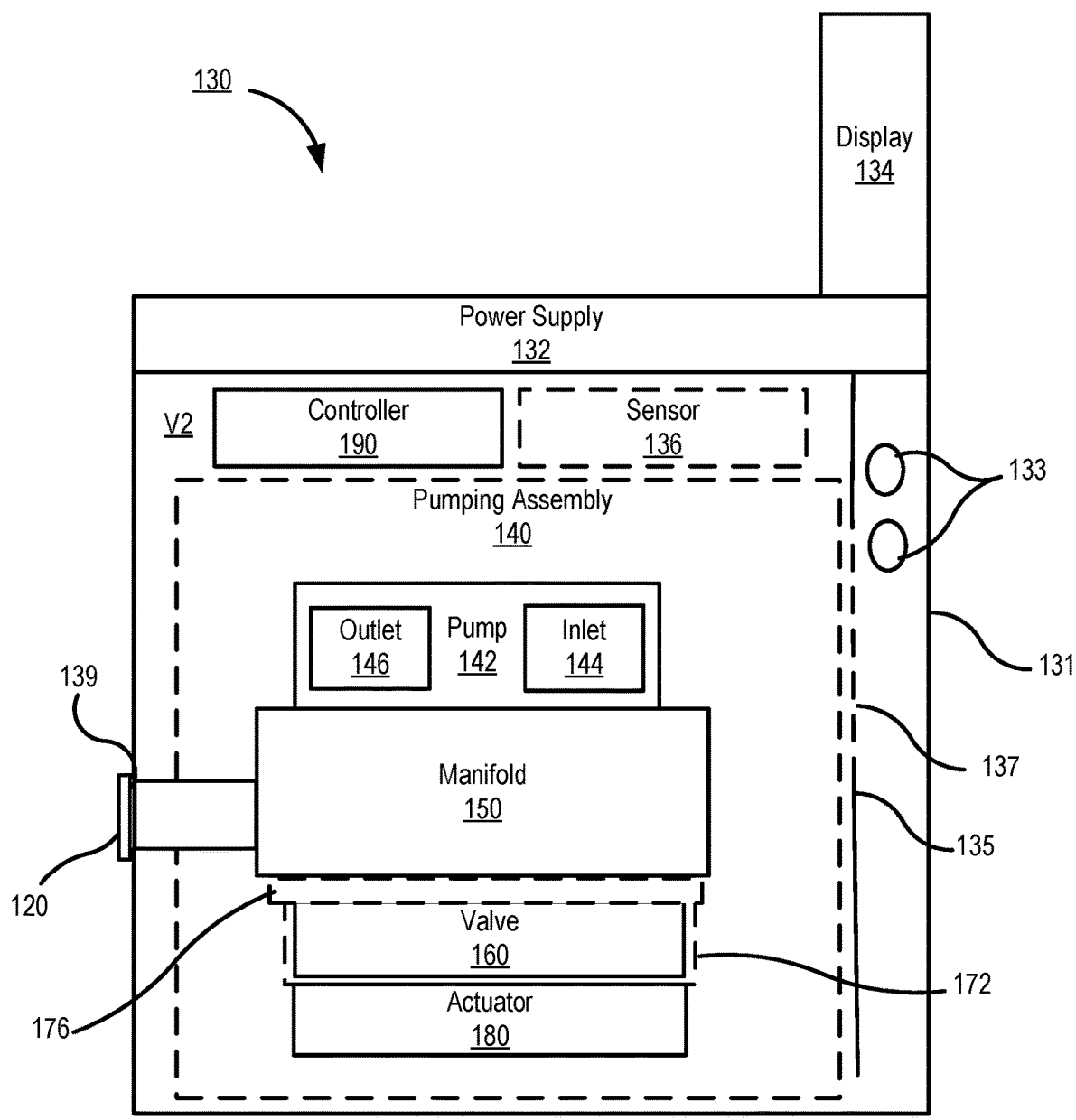
FIG. 3 is a schematic illustration of the ventilator included in the system of FIG. 1.

FIG. 3 is a schematic illustration of the ventilator 130 that may be included in the system 100. The ventilator 130 is fluidically coupled to the cuirass 102 so as to be in fluidic communication with the first internal volume V1. The ventilator 130 may include the housing 131, a pumping assembly 140 including a pump 142, a valve 160, an actuator 180, and optionally, a manifold 172, and a gasket 176. The ventilator 130 may also include a power supply 132, a display 134, a controller 190 and optionally, a sensor(s) 136.

The housing 131 defines a second internal volume V2 within each at least some components of the ventilator 130 are disposed. The housing 131 defines at least one opening 133 to allow air to flow into an out of the second internal volume V2. For example, the at least one opening 133 may include slots, cutouts, through-holes, or apertures having any suitable shape (e.g., circular, oval, elliptical, square, rectangular, polygonal, any other suitable shape or combination thereof) and/or size (e.g., diameter) to allow air to flow into and out of the second internal volume V2. In some embodiments, the housing 131 may also include a wall 135 disposed in the second internal volume V2 and separating the second internal volume V2 into a first portion that is fluidically coupled to an external environment through the housing 131 (e.g., via the at least one opening 133), and a second portion within which at least some of the components of the ventilator 130 (e.g., the pumping assembly 140, the controller 190, and the sensor(s) 136) are disposed. The wall 135 defines multiple openings 137 therethrough through which air can pass between the first portion and the second portion of the second internal volume V2. In some embodiments, the multiple openings 137 may cause the wall 135 to serve as a muffler or silencer configured to reduce a sound level as air passed between the first portion and the second portion. In some embodiments, an aperture 139 may be defined in the sidewall of the housing 131 through which the flow member 120 is coupled to the pumping assembly 140 (e.g., fluidically and optionally, physically coupled to the manifold 150).

The power supply 132 may include any suitable power storage system or device (e.g., a battery, electrochemical cell, electrical leads, etc.) configured to store electrical power and provide electrical power to various components of that that ventilator 130 (e.g., the pump 142, the actuator 180, the controller 190, the sensor(s) 136, and/or the display 134. In some embodiments, the housing 131 may define a power supply receptacle in which the power supply 132 or at least a power storage device (e.g., a battery) of the power supply 132 may be removably disposed. The power storage device of the power supply 132 may be rechargeable (e.g., Li-ion battery, a NiCad battery, etc.), or disposable. In embodiments in which the power storage device is rechargeable, the ventilator 130 may include an electrical plug to enable electrical coupling of the power supply 132 with an external power supply (e.g., a wall outlet). In some embodiments, solar panels may be provided on the ventilator 130 to convert solar energy into electrical energy for charging the power storage device of the power supply 132.

The display 134 may be disposed on and coupled to the housing 131 such that the display 134 is viewable to the user U when the cuirass 102 and thereby, the ventilator 130 is disposed on the thorax T of the user U. In some embodiments, the display 134 may be hingedly coupled to housing 131 such that the user U may selectively rotate the display 134 into a first orientation in which the display 134 is disposed away from the housing 131 when the user U intends to view or engage the display 134, and rotate display 134 into a second orientation in which the display is proximate to the housing 131 (e.g., folded flat against a surface of the housing 131 or disposed in a corresponding receptacle defined in the housing 131) when the user U does not intend to engage the display 134. In some embodiments, the display 134 may be configured to automatically turn OFF (e.g., enter a hibernation mode) when the display 134 is in the second orientation, and to automatically turn ON when display 134 is moved into the first orientation.

In some embodiments, the display 134 may include a touchscreen which may be engaged by the user to input various command to the ventilator 130 (e.g., activate/deactivate pump, adjust air pressure, adjust inhalation/exhalation cycle time, select parameters to be displayed on the display 134, etc.). In some embodiments, a physical button or switch may be provided on the display 134 or another portion of the housing 131 that is configured to be engaged by the user U to activate/deactivate the ventilator 130.

In some embodiments, the display 134 may be fixedly coupled to the housing 131 and may be communicatively coupled to the controller 190 via a wired connection. In some embodiments, the display 134 may be removably coupled to the housing 131 and may be communicatively coupled to the controller 190 via removable wired connection, or a wireless connection (e.g., via a half-transceiver, a full-duplex transceiver, an RF transceiver, an optical transceiver, BLUETOOTH® transceiver, a WI-FI® transceiver, a near field communication (NFC) transceiver, etc.). In some embodiments, instead of including a display, the housing 131 may including a mounting structure (e.g., clips or clamps that may be adjustable, magnets, or any other suitable mounting structure) structured or configured to mount a user device (e.g., a mobile phone or a tablet) on the housing 131. In such embodiments, an application or API may be installed on the user device that is configured to communicate with the controller 190 via a wired or wireless connection and configured to perform the one or more aforementioned functions of the display and/or to allow the user to control or adjust operations of the ventilator 130. In such embodiments, the ventilator 130 may include a charging plug that is inserted into the user device when the user device is mounted on the housing 131 (e.g., to charge the user device or allow the controller 190 to communicate therewith), or may include a charging port (e.g., a USB-A, USB-B, USB-B mini, USB-B micro, USC-C, or a lightning port or any other charging port) to allow the user to communicatively couple the ventilator 130 to the user device via a charging and/or communication cable.

The pump 142 is disposed within the second internal volume V2 and includes an inlet 144 configured to draw or suck air into the pump 142, and an outlet 146 configured to expel pressurized air out the pump 142. Any suitable pump may be used. In some embodiments, the pump 142 may include a centrifugal pump, a blower, a peristaltic pump, a vacuum pump, any other suitable pump, or a combination thereof.

The valve 160 is disposed in the second internal volume V2 and configured to be moved between a first configuration during exhalation in which the outlet 146 of the pump 142 is fluidically coupled to the first internal volume V1 and the inlet 144 of the pump 142 is coupled to the second internal volume V2 via the valve 160, and a second configuration during inhalation in which the outlet 146 of the pump 142 is fluidically coupled to the second internal volume V2 and the inlet 144 of the pump 142 is fluidically coupled to the first internal volume V1 via the valve 160. The actuator 180 is operatively coupled to the valve 160 and configured to move the valve 160 between the first configuration and the second configuration. The actuator 180 may include a motor (e.g., a stepper motor, a linear motor, a servo motor, any other suitable matter or combination thereof), a solenoid, a linear actuator, a rack and pinion drive, a pulley, any other suitable actuator or a combination thereof.

In some embodiments, the valve 160 may include a rotational valve such that the first configuration is a first angular orientation and the second configuration is a second angular orientation. In such embodiments, the actuator 180 is configured to rotate the valve 160 about a central axis of the valve 160 in a first rotational direction to place the valve 160 in the first angular orientation, and in a second rotational direction opposite the first rotational direction to place the valve 160 in the second angular orientation. For example, the actuator 180 may include a shaft disposed at least partially through a central channel defined through the valve 160 and coupled thereto so as to rotationally lock the shaft of the actuator 180 with the valve 160. In some embodiments, the shaft may include a flat portion inserted within a corresponding flat portion of the valve 160 to rotationally lock the valve 160 to the shaft of the actuator 180. In some embodiments, the actuator 180 rotates the valve approximately 90 degrees about the central axis between the first angular orientation and the second angular orientation.

In some embodiments, instead of moving the valve 160 in opposite rotational directions to move the valve 160 between the first angular orientation and the second angular orientation, the actuator 180 may be configured to move the valve 160 in the same rotational direction to move the valve 160 between the first and second angular orientations. For example, the actuator 180 may rotate the valve 160 in one of a clockwise or anticlockwise direction (e.g., by an angle of about 90 degrees) to move the valve 160 into the first angular orientation (e.g., during exhaling by the user U). The actuator 180 may then rotate the valve 160 in the same one of the clockwise or anticlockwise direction (e.g., by an angle of about 90 degrees) to move the valve 160 into the second angular orientation, and so on and so forth. In such embodiments, the actuator 180 may include, for example, a stepper motor configured to rotate the valve 160 in predetermined steps to move the valve 160 between the first and second configurations.

Figure 4A:
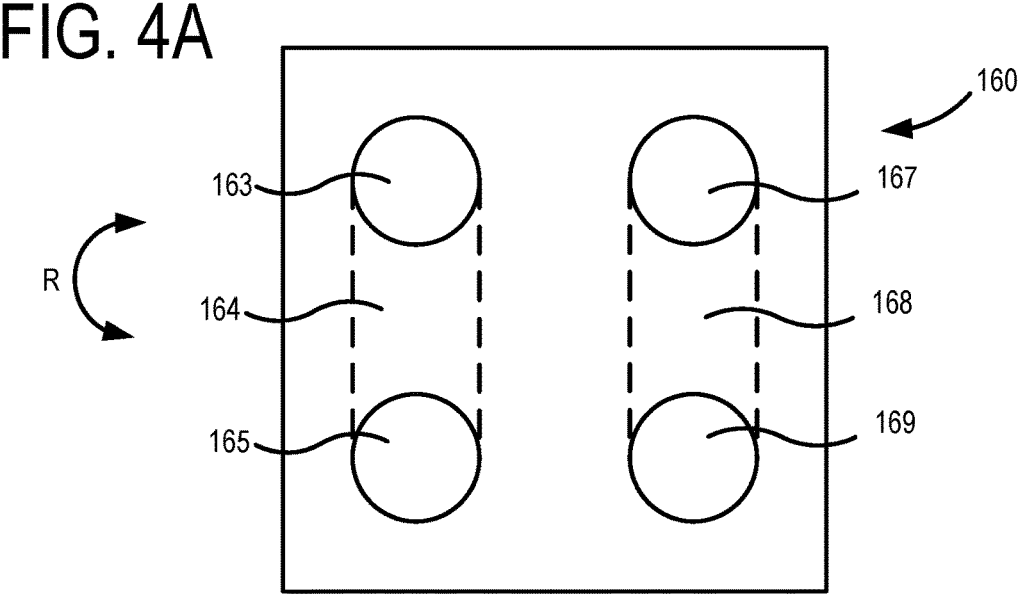
FIG. 4A is a top view of a valve included in the ventilator of FIG. 3, and FIGS. 4B and 4C are side views of the valve fluidically coupled to a manifold and a pump of the ventilator with the valve being in a first configuration.
Figure 5A:
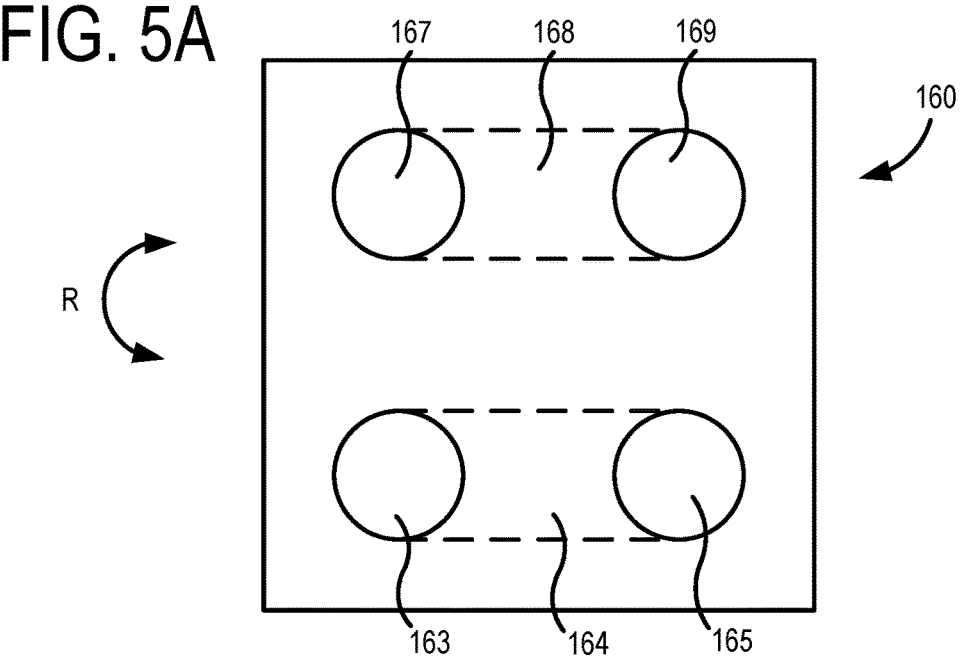
FIG. 5A is a top view of a valve included in the ventilator of FIG. 3, and FIGS. 5B and 5C are side views of the valve fluidically coupled to a manifold and a pump of the ventilator with the valve being in a second configuration.

Expanding further, FIGS. 4A and 5A are top views of the valve 160 in the first configuration and the second configuration, respectively. The valve 160 may include a first flow path 164 and a second flow path 168 such that in the first configuration (e.g., the first angular orientation) of the valve 160, the first flow path 164 fluidically couples the outlet 146 of the pump to an inlet of the cuirass 102 (e.g., the flow member 120) and thus the first internal volume V1, and the second flow path 168 fluidically couples the inlet 144 of the pump 142 to the external environment through the second internal volume V2. Moreover, in the second configuration (e.g., the second angular orientation) of the valve 160, the first flow path 164 fluidically couples the inlet 144 to the inlet of the cuirass and thus the first internal volume V1, and the second flow path 168 fluidically couples the outlet 146 to the external environment through the second internal volume V2. The valve 160 may be configured to have an operational life of millions of cycles (e.g., greater than 1 million, greater than 2 million, greater than 3 million, greater than 4 million, greater than 5 million, greater than 6 million, greater than 7 million, greater than 8 million, greater than 9 million, greater than 10 million, or even higher), thus reducing maintenance cost and increasing lifetime of the ventilator 130.

The valve 160 may have any suitable shape or profile, for example, circular, square, elliptical, oval, etc., such that the valve 160 is movable between the first configuration (e.g., the first angular orientation) and the second configuration (e.g., the second angular orientation). The valve 160 may include a single piece formed via forging, casting, machining, any other suitable method, or any suitable combination thereof. In some embodiments, the valve 160 may have a circular shape. As shown in FIGS. 4A and 5A, the first flow path 164 fluidically couples a first opening 163 defined by the valve 160 to a second opening 165 defined by the valve 160, and the second flow path 168 fluidically couples a third opening 167 defined by the valve 160 to a fourth opening 169 defined by the valve 160. Each of the first opening 163, the second opening 165, the third opening 167, and the fourth opening 169 are defined on a single planar surface of the valve 160, for example, a surface that faces the pump 142.

In some embodiments, the valve 160 may be fluidically coupled to the inlet 144 and the outlet of the pump 146 in the first and second angular orientations through the manifold 150. Referring also to FIGS. 4B-4C, and 5B-5C, the manifold 150 may be coupled to the pump 142 (e.g., fluidically and optionally, physically coupled), for example, via fasteners such as screws, nuts. bolts, rivets, etc. In some embodiments, the manifold 150 may define one or more receptacles within which at least a portion of the pump 142 may be disposed and secured thereto, for example, via friction fit, snap fit, clips, clamps, and/or fasteners. In some embodiments, the manifold 150 may include a single piece that is molded, casted, or machined so as to define multiple channels therein. For example, the manifold 150 may include a first channel 152 fluidically coupled to the outlet 146 of the pump 142, a second channel 154 fluidically coupled to the first internal volume V1 defined by the cuirass 102, a third channel 156 fluidically coupled to a volume external to the manifold 150 (e.g., the second internal volume V2), and a fourth channel 158 fluidically coupled to the inlet 144 of the pump 142.

The first channel 152 may define a first receptacle in which at least a portion of the outlet 146 of the pump 142 is received. The second channel 154 may by coupled to the flow member 120 (e.g., via threads, snap-fit, friction fit, clips, clamps, etc.). In some embodiments, the second channel 154 may extend radially out of the housing 131 towards the aperture 139 defined in the housing 131, and may abut against an inner surface of the wall of the housing 131 in which the aperture 139 is defined or extend out of the aperture 139 for coupling to the flow member 120. In such embodiments, a gasket or O-ring may be disposed between the second channel 154 and the corresponding wall of the housing 131 to fluidically seal the aperture 139. In some embodiments, the first portion of the flow member 120 may extend into the second internal volume V2 of the housing 131 and be coupled to the second channel 154 of the manifold 150 that may be located within the second internal volume V2. In such embodiments, the gasket or O-ring may be disposed between a surface of the flow member 120 (e.g., a distal surface of the second portion) and an outer surface of the wall of the housing 131 in which the aperture 139 is defined. The third channel 156 is exposed to the second internal volume V2, and the fourth channel 158 may define a second receptacle in which at least a portion of the inlet 144 is received.

Figure 4B:
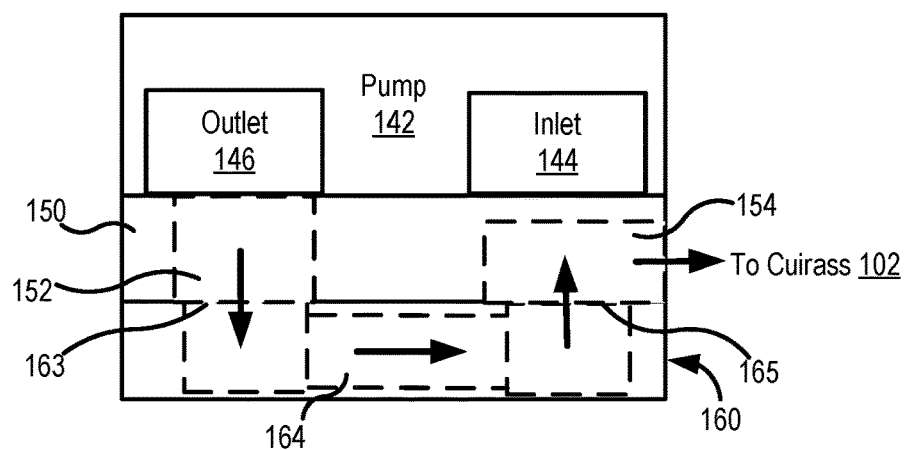
Figure 4C:
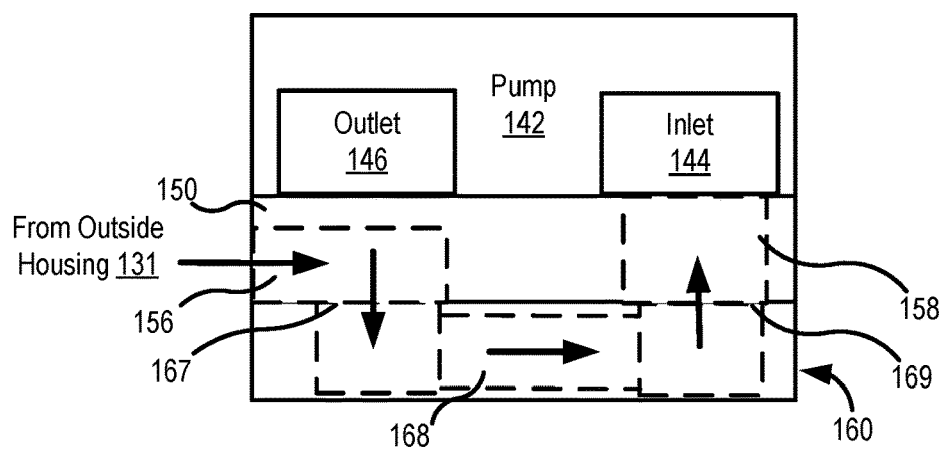

In the first angular orientation as shown in FIGS. 4A-4C, the valve 160 is oriented by the actuator 180 (e.g., based on a command or instruction received from the controller 190) by rotating the valve 160 in the first rotational direction indicated by the arrow R (e.g., one of a clockwise or anti-clockwise direction) such that the first opening 163 is axially aligned with the first channel 152, the second opening 165 is axially aligned with the second channel 154, the third opening 167 is axially aligned with the third channel 156, and the fourth opening 169 is axially aligned with the fourth channel 158. Thus, in the first angular orientation, the first flow path 164 fluidically couples the first channel 152 and the thereby, the outlet of the pump 146, to the second channel 154 and thereby, the first internal volume V1 of the cuirass 102. Moreover, the second flow path 168 fluidically couples the third channel 156 and thereby, the second internal volume V2, to the fourth channel 158 and thereby, the inlet 144. Thus, in the first angular orientation which corresponds to the user U exhaling, a positive pressure is applied on the first internal volume V1 because of the outlet 146 of the pump 142 being fluidically coupled to thereto. In the first angular orientation, air flows from outside the housing 131 flows through the second internal volume V2 into the inlet 144 via the third channel 156, the second flow path 168, and the fourth channel 158, respectively, and then into the first internal volume V1 of the cuirass 102 from the outlet 146 via the first channel 152, the first flow path 164, and the second channel 154, respectively.

Figure 5B:
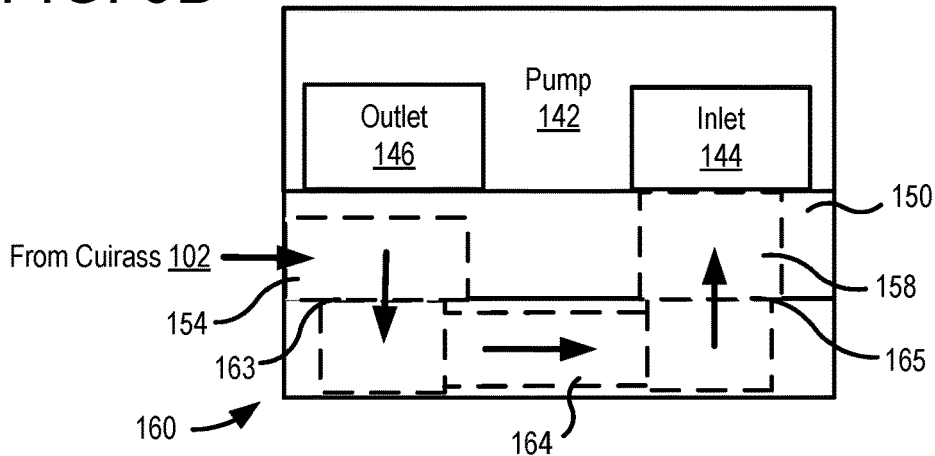
Figure 5C:
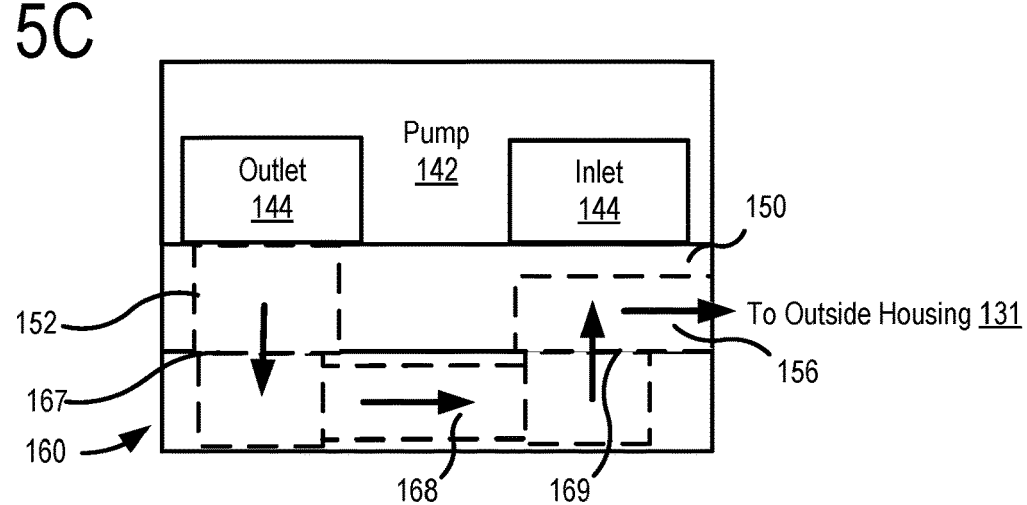

FIG. 5A is a top view of the valve 160, and FIGS. 5B and 5C are side views of the valve 160 coupled to the manifold 150 in the second angular orientation corresponding to the user U inhaling. For example, the valve 160 is oriented by the actuator 180 (e.g., based on a command or instruction received from the controller 190) by rotating the valve 160 in the second rotational direction opposite the first rotational direction indicated by the arrow R (e.g., the other of the clockwise or anti-clockwise direction) such that the first opening 163 is now axially aligned with the second channel 154, the second opening 165 is axially aligned with the fourth channel 158, the third opening 167 is axially aligned with the first channel 152, and fourth opening 169 is axially aligned with the third channel 156. Thus, in the second angular orientation, the first flow path 164 fluidically couples the second channel 154 and thereby, the first internal volume V1 of the cuirass 102, to the fourth channel 158, and thereby the inlet 144 of the pump 142. Moreover, the second flow path 168 fluidically couples the first channel 152 and thereby, the outlet 146 of the pump 142, to the third channel 156 and thereby, the second internal volume V2 and thereby, the external environment outside the housing 131. Thus, in the second angular orientation which corresponds to the user U inhaling, a negative pressure is applied on the first internal volume V1 because of the inlet 144 of the pump 142 being fluidically coupled to thereto. In the second angular orientation, air flows from the first internal volume V1 via the second channel 154, the first flow path 164 and the fourth channel 158 into the pump inlet 144, thereby removing air from the first internal volume V1. Moreover, air flows from the outlet 146 of the pump 142 through the first channel 152, the second flow path 168, and the third channel 156 to the second internal volume V2 and subsequently, out of the housing 131.

Although not shown in FIGS. 4A-5C, in some embodiments, the actuator 180 (e.g., based on a command or instruction received from the controller 190) can be configured to place the valve 160 in a third or intermediate angular orientation. For example, the valve 160 is shown in FIGS. 4A and 5A as being rotated 90° relative to the manifold 150 to transition from the first angular orientation to the second angular orientation. In contrast, in some instances, the actuator 180 may be configured to rotate the valve 45° relative to the manifold 150 to place the valve 160 into the third or intermediate angular orientation. In some such embodiments, the arrangement of the manifold 150 and the valve 160 can be such that the openings 163, 165, 167, and 169 of the valve 160 are in fluid communication with two of the channels 152, 154, 156, and 158 of the manifold. For example, the openings 163, 165, 167, and 169 may be misaligned and/or otherwise non-coaxial with the channels 152, 154, 156, and 158 (e.g., disposed between adjacent channels 152, 154, 156, and 158), and can be of sufficient size to allow the openings 152, 154, 156, and 158 to be in fluid communication with at least two adjacent channels 163, 165, 167, and 169. In some implementations, placing the valve 160 in the third angular orientation can act as a shunt, bypass, diverter, and/or the like that diverts or redirects at least a portion of the flow of air between the pump 142 and at least the first internal volume V1 of the cuirass 102. In some implementations, placing the valve 160 in the third angular orientation can allow the pump 142 to continue to run without providing respiratory assistance or providing only limited respiratory assistance. In some implementations, placing the valve 160 in the third angular orientation while the valve 160 is otherwise transitioning between the first and second angular orientations (e.g., for a very short period) can smooth a transition between providing the first internal volume V1 with positive pressure and negative pressure (or vice versa), which may increase comfort for the user U.

Referring to FIG. 3, the pumping assembly 140 may also include a valve body 172 within which the valve 160 is disposed. For example, the valve body 172 can have an interior surface defining a cavity such that the valve 160 is movably disposed in the cavity between the first angular orientation and the second angular orientation. In some embodiments, the cavity may have a shape that corresponds to a shape of the valve 160 such that the valve 160 is snugly disposed in the cavity while having sufficient clearance between the interior surface of the valve body 172 and a corresponding exterior surface of the valve 160 to enable the valve 160 to move freely within the cavity between the first and second angular orientations.

In some embodiments, the interior surface of the valve body 172 may form a first notch and a second notch offset from the first notch, for example, offset by an angle of about 90 degrees, and the valve 160 may have a projection formed on a surface thereof, for example, protruding from an outer radial surface thereof. The first and second notch may be located such that the projection is at least partially disposed in the first notch when the valve 160 is in the first configuration and at least partially disposed in the second notch when the valve 160 is in the second configuration. The projection, and the first and second notches may serve as a motion stops to limit the motion of the valve 160 as it rotates between the first and second angular orientations, and to ensure that each of the first opening 163, the second opening 165, the third opening 167, and the fourth opening 169 of the valve 160 are aligned with corresponding one of the first channel 152, the second channel 154, the third channel 156, or the fourth channel 158 of the manifold 150, as previously described herein in the first and second angular orientations. Thus, the first and second notches and the corresponding projection of the valve 160 may ensure alignment between the valve 160 and the manifold 150, and thereby, the pump 142 over millions of operational cycles of the valve 160. In some embodiments, the valve body 172 may define an opening, for example, through a base of the cavity through which the actuator 180 is coupled to the valve 160. For example, the valve body 172 may define a central opening through a base thereof, through which a shaft of the actuator 180 protrudes and is inserted into a corresponding central channel of the valve 160 or otherwise coupled thereto, as previously described herein.

In some embodiments, a gasket 176 may be disposed between the valve 160 and the manifold 150. The gasket 176 can be configured to form a seal between the valve 160 and the manifold 150 in each of the first angular orientation and the second angular orientation of the valve 160. For example, the gasket 176 may include a flat sheet of a resilient material (e.g., rubber, silicone, polymers, ceramics, any other suitable material or a combination thereof) that defines a plurality of through-holes that correspond to the locations of the first opening 163, the second opening 165, the third opening 167, and the fourth opening 169, respectively. The first opening 1643, the second opening 165, the third opening 167, and the fourth opening 169 may defined symmetrically about a central axis of the valve 160 (e.g., located at the same radial distance from the central axis of the of the valve 160, and radially spaced apart at an angle of about 90 degrees from each other. Thus, each of the first opening 163, the second opening 165, the third opening 167, and the fourth opening 169 is axially aligned with one of the plurality of through-holes of the gasket 176 in each of the first and second angular orientations, and therethrough, to the corresponding one of the channels 152, 154, 156, or 158 of the manifold 150, as previously described herein.

In some embodiments, at least one of the valve body 172 or the actuator 180 is configured to rotate the valve 160 such that a surface of the valve 160 that faces the gasket 176 remains in contact with the gasket 160 during rotation of the gasket 176. In some embodiments, at least one of the valve body 172 or the actuator 180 is configured to rotate the valve 160 such that the surface of the valve 160 only contacts the gasket 176 once the valve 160 is in the first angular orientation or the second angular orientation. For example, the cavity of the valve body 172 may be structured and/or the actuator 180 may be configured to move the valve 160 axially away from the gasket 176 and then rotate the valve from the first angular orientation to the second angular orientation or vice versa. Once the valve 160 is in the desired angular orientation (e.g., the first angular orientation or the second angular orientation), the valve body 172 and/or the actuator 180 may be configured to move the valve 160 axially towards the gasket 176 until the surface of the valve 160 contacts the gasket 176. This type of motion may inhibit sliding of the surface of the valve 160 against the gasket 176 during rotation of the valve 160, thereby reducing wear of the gasket 176 and increasing lifetime.

It should be appreciated that while the valve 160, the manifold 150, the valve body 172, the gasket 176, and the actuator 180, are described as separate components, in some embodiments, the aforementioned components may be integrated together in a valve assembly configured to be coupled to the pump 142.

In some embodiments, the ventilator 130 may include a sensor(s) 136 configured to measure one or more parameters of the ventilator 130 and/or the user U. In some embodiments, the sensor(s) 136 may include a pressure sensor (e.g., a positive or negative pressure sensor, a differential pressure sensor (delta-P sensor), a MEMS sensor, a piezoelectric sensor, a capacitive sensor, any other suitable pressure sensor, or a combination thereof) configured to determine the pressure within the first internal volume V1 of the cuirass 102 and generate a pressure signal indicative of the pressure within the first internal volume V1. In such embodiments, the sensor(s) 136 or at least a portion thereof may be disposed in the first internal volume V1 and be in communication with the controller 190 through a wired or wireless connection. In some embodiments, the sensor(s) 136 may be configured to measure one or more physiological parameters of the patient. For example, the sensor(s) 136 may include a contact sensor, an ECG electrode, a heart rate sensor, a PPG sensor, a blood pressure sensor, a blood oxygen sensor, any other suitable sensor, or a combination thereof, that is configured to measure one or more physiological parameters of the user U. In some embodiments, the sensor(s) 136 may include an airflow sensor configured to measure flow rate or velocity of air entering or exiting the first internal volume V1. In some embodiments, the sensor(s) 136 may include a volume sensor configured to detect a change in volume of the air within the first internal volume V1. In some embodiments, the sensor(s) 136 may include a temperature sensor configured to measure a temperature of the user U or a temperature inside the first internal volume V1, for example, to enable more accurate calculation of the first internal volume V1. In some embodiments, the sensor(s) 136 may include an acoustic sensor configured to detect sound and/or changes in characteristics of a sound (e.g., pitch, volume, etc.). In some embodiments, the sensor(s) 136 may include and/or may employ strain gauge(s) or the like configured to detect electrical resistance associated with an amount of strain along a detector. In some embodiments, the sensor(s) 136 may include any sensor as described in the '740 application and all such sensors should be considered to be within the scope of this disclosure.

The controller 190 is in communication with the actuator 180 and may also be in communication with the pump 142, the sensor(s) 136, and/or the display 134. The controller 190 is configured to control the operations of the ventilator 130. For example, the controller 190 may be configured to activate the pump 142 (e.g., based on an input received from the user U such as via the display 134), determine a pressure within the first internal volume V1 based on a pressure signal received from the sensor(s) 136, and/or control operation of the actuator 180 to move the valve 160 between the first configuration (e.g., the first angular orientation) and the second configuration (e.g., the second angular orientation).

For example, the controller 190 may be determine that the user U is exhaling (e.g., based on a pressure signal received from the sensor(s) 136) and responsive to the determining that the user is exhaling, cause the actuator 180 to move the valve 160 into the first configuration (e.g., the first angular orientation) in which the first flow path 164 fluidically couples the outlet 146 of the pump 142 to the first internal volume V1 of the cuirass 102, and the second flow path 168 fluidically couples the inlet 144 of the pump 142 to the second internal volume V2, as previously described herein. Moreover, the controller 190 may determine that the user U is inhaling (e.g., based on a pressure signal from the sensor(s) 136), and responsive to determining that the user U is inhaling, cause the actuator 180 to move the valve 160 into the second configuration (e.g., the second angular orientation) in which the first flow path 164 fluidically couples the inlet 144 of the pump 142 to the first internal volume V1 and the second flow path 168 fluidically couples the outlet 146 of the pump 142 to the second internal volume V2.

In some embodiments, the controller 190 may be configured to cause the actuator 190 may be configured to move from the first configuration and the second configuration and vice versa at predetermined time intervals corresponding to a time period corresponding to the user U exhaling or inhaling, respectively. In such embodiments, the ventilator 130 may not include a pressure sensor. The predetermined time intervals may be input by the user U, or may be determined by a medical professional (e.g., based on prior breathing tests performed on the user U by the medical professional), and communicated to the controller 190 via the display 134 or wirelessly communicated to the controller 190 from a remote device via a communication network (e.g., any suitable Local Area Network (LAN), Wide Area Network (WAN), Wireless Personal Area Network (WPAN), which may be supported by Frequency Division Multiple Access (FDMA), Time Division Multiple Access (TDMA), Code Division Multiple Access (CDMA) (particularly, Evolution-Data Optimized (EVDO)), Universal Mobile Telecommunications Systems (UMTS) (particularly, Time Division Synchronous CDMA (TD-SCDMA or TDS) Wideband Code Division Multiple Access (WCDMA), Long Term Evolution (LTE), evolved Multimedia Broadcast Multicast Services (eMBMS), High-Speed Downlink Packet Access (HSDPA), and the like), Universal Terrestrial Radio Access (UTRA), Global System for Mobile Communications (GSM), Code Division Multiple Access 1× Radio Transmission Technology (1×), General Packet Radio Service (GPRS), Personal Communications Service (PCS), 802.11X, ZigBee, Z-Wave, Bluetooth, Wi-Fi, any suitable wired network, combination thereof, and/or the like). In some embodiments, the controller 190 may also be configured to communicate information to the cloud server or remote server, for example, the provide real time or periodic monitoring of the physiological parameters of the user U, operational parameters and/or usage information of the ventilator 130 to the medical professional.

In some embodiments, the controller 190 may be configured to adjust various operations of the ventilator 130, for example, based on an input received from the user U. Such operations may include, but are not limited to activating/deactivating the pump 142, adjusting a speed or power of the pump 142 (e.g., to control a pressure of the air being communicated into or out of the first internal volume V1), adjusting a movement (e.g., rotation) speed or frequency of the actuator 180 and thereby, the valve 160 between the first and the second configurations, ventilator or user parameters being displayed on the display 134, etc. In some embodiments, the controller 190 may be configured to perform any of the operations as described in the '740 application and all such operations should be considered to be within the scope of this disclosure.

Figure 6:
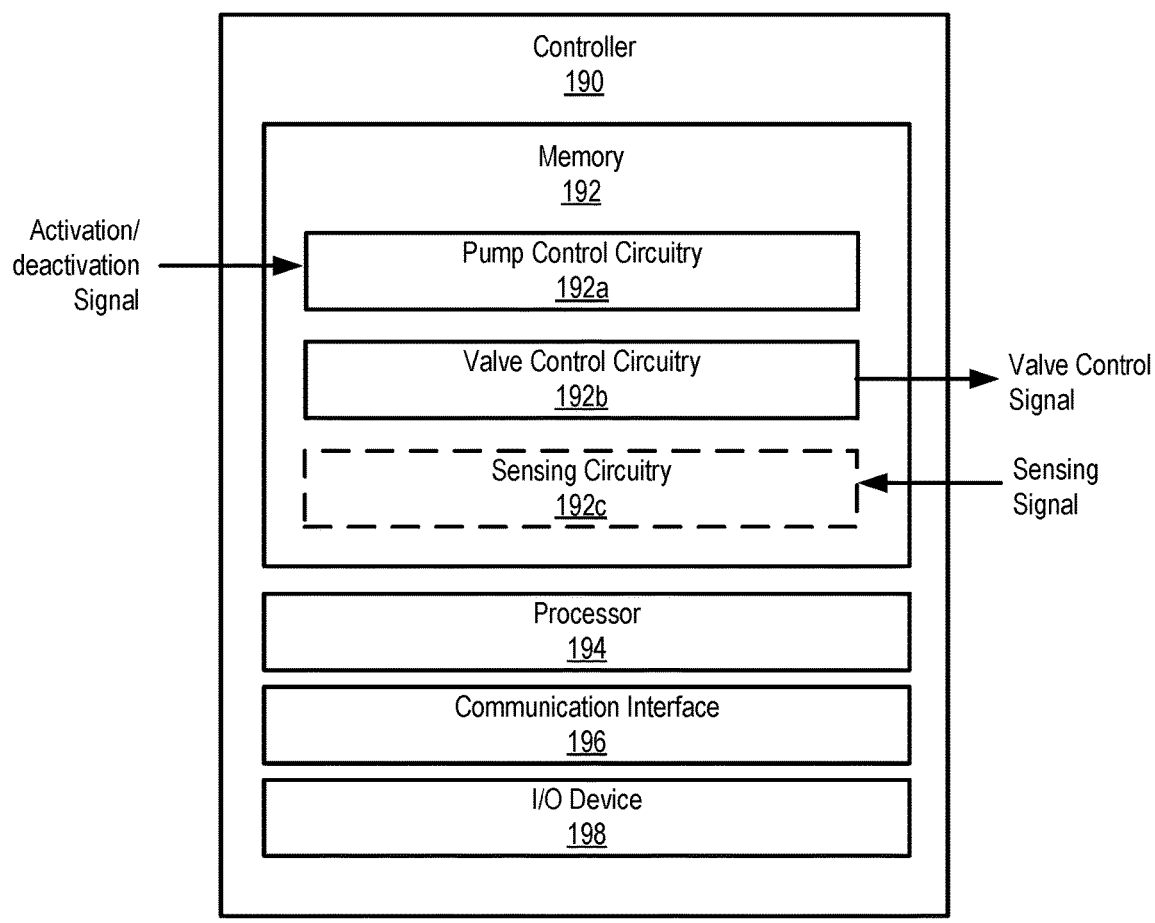
FIG. 6 is a schematic block diagram of a controller that may be included in the ventilator of FIG. 3, according to an embodiment.

FIG. 6 is a schematic block diagram of the controller 190 that may be included in the ventilator 100. While FIG. 6 illustrates a particular implementation of the controller 190, any other suitable controller or control unit configured to perform the operations described herein may be used. In some implementations, portions and/or functions of the controller 190 may be performed and/or executed on or by a remote device such as a personal computer, tablet, smartphone, wearable device, digital assistant hub or device, and/or the like. Such a remote device can be in communication with the controller 190 via any suitable network or communication modality such as those described herein.

The controller 190 can include a memory 192, a processor 194, a communication interface 196, and an input/output (I/O) interface 198. The memory 192 can be any suitable memory device(s) configured to store data, information, computer code or instructions (such as those described herein), and/or the like. In some embodiments, the memory 192 can be and/or can include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory 192 can store instructions to cause the processor 194 to execute modules, processes, and/or functions associated with the system 100, such as models, calculations, or other algorithms to analyze or determine pressure within the first internal volume and control operation of the valve 160 accordingly. In some embodiments, the memory 192 may also be configured to at least temporarily pressure data, operational data associated with the operation of the ventilator, and/or physiological data associated with the user U.

The processor 194 can be any suitable processing device(s) configured to run and/or execute a set of instructions or code. For example, the processor 194 can be and/or can include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or the like. The processor 194 can be, for example, a general-purpose processor, central processing unit (CPU), microprocessor, microcontroller, Field Programmable Gate Array (FPGA), an Application Specific Integrated Circuit (ASIC), a processor board, a virtual processor, and/or the like. The processor 194 can be configured to run and/or execute application processes and/or other modules, processes and/or functions associated with the ventilator 130. The underlying device technologies may be provided in a variety of component types, for example, metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like. In some embodiments, the processor 194 can be configured to receive data from sensor(s) 136, the display, or other components of the ventilator 130 and to process that data, for example, to determine the pressure within the first internal volume V1 for moving the valve 160 between the first and second configurations.

The communication interface(s) 196 can be any suitable device(s) and/or interface(s) that can communicate with the sensor(s), the actuator 180, the power supply 132, and/or display 134, and in some embodiments, a network (e.g., a local area network (LAN), a wide area network (WAN), or the cloud), or an external device (e.g., a user device such as cell phone, tablet, a laptop, or a desktop computer, etc.). Moreover, the communication interface(s) 196 can include one or more wired and/or wireless interfaces, such as, for example, Ethernet interfaces, optical carrier (OC) interfaces, and/or asynchronous transfer mode (ATM) interfaces. In some embodiments, the communication interface(s) 196 can be, for example, a network interface card and/or the like that can include at least an Ethernet port and/or a wireless radio (e.g., a WI-FI® radio, a BLUETOOTH® radio, cellular such as 3G, 4G, 5G, etc., 802.11X Zigbee, Z-Wave, etc.). In some embodiments, the communication interface(s) 196 can include one or more satellite, WI-FI®, BLUETOOTH®, or cellular antenna. In some embodiments, the communication interface(s) 196 can be communicably coupled to an external device (e.g., an external processor) that includes one or more satellite, WI-FI®, BLUETOOTH®, or cellular antenna, or the power supply 132. The communication interface(s) 196 may also be configured to communicate signals to the actuator 180, the pump 142 and/or the display 134.

The I/O device(s) 198 may include any suitable device to receive input from the user U or communicate an output to the user U, for example, via the display 134. In some embodiments, the I/O device(s) 198 may include an activation mechanism or otherwise, a user actuated element (e.g., a touch button, a push button, a switch, a touchpad, etc.) to turn on or otherwise, activate the ventilator 130, or to allow the user to enter information, request information, or set various parameters of the ventilator 130. In some embodiments, the I/O device(s) 198 may include a visual indicator (e.g., LED lights) to display information to the user U (e.g., corresponding to the ventilator 130 being activated or corresponding to, or communicated information to the display 134 for displaying to the user U.

In some embodiments, the controller 190 may include various circuitries implemented in hardware or software configured to perform the operations of the controller 190. For example, as shown in FIG. 6, the controller 190 includes a pump control circuitry 192a, a valve control circuitry 192b, and optionally, a sensing circuitry 192c. The processes performed by these circuitries were described above with reference to the controller 130.

In one configuration, the pump control circuitry 192a, the valve control circuitry 192b, and the sensing circuitry 192c can be embodied as machine or computer-readable media (e.g., stored in the memory 192) that is executable by a processor, such as the processor 194. As described herein and amongst other uses, the machine-readable media (e.g., the memory 192) facilitates performance of certain operations of the pump control circuitry 192a, the valve control circuitry 192b, and the sensing circuitry 192c to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). Thus, the computer readable media may include code, which may be written in any programming language including, but not limited to, Java, Python, and/or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, wireless network, etc.).

In another configuration, the pump control circuitry 192a, the valve control circuitry 192b, and the sensing circuitry 192c may include circuitry components including, but not limited to, processing circuitry, network interfaces, peripheral devices, input devices, output devices, sensors, etc. In some embodiments, the pump control circuitry 192a, the valve control circuitry 192b, and the sensing circuitry 192c may take the form of one or more analog circuits, electronic circuits (e.g., integrated circuits (IC), discrete circuits, system on a chip (SOC) circuits, microcontrollers, etc.), telecommunication circuits, hybrid circuits, and any other type of "circuit." In this regard, the pump control circuitry 192a, the valve control circuitry 192b, and the sensing circuitry 192c may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on.

Thus, the pump control circuitry 192a, the valve control circuitry 192b, and the sensing circuitry 192c may also include programmable hardware devices such as field programmable gate arrays, programmable array logic, programmable logic devices or the like. In this regard, the pump control circuitry 192a, the valve control circuitry 192b, and the sensing circuitry 192c may include one or more memory devices for storing instructions that are executable by the processor(s) of the pump control circuitry 192a, the valve control circuitry 192b, and the sensing circuitry 192c. The one or more memory devices and processor(s) may have the same definition as provided below with respect to the memory 192 and the processor 194.

In the example shown, the controller 190 includes the processor 194 and the memory 192. The processor 194 and the memory 192 may be structured or configured to execute or implement the instructions, commands, and/or control processes described herein with respect to the pump control circuitry 192a, the valve control circuitry 192b, and the sensing circuitry 192c. Thus, the depicted configuration represents the aforementioned arrangement in which the pump control circuitry 192a, the valve control circuitry 192b, and the sensing circuitry 192c are embodied as machine or computer-readable media. However, as mentioned above, this illustration is not meant to be limiting as the present disclosure contemplates other embodiments such as the aforementioned embodiment in the pump control circuitry 192a, the valve control circuitry 192b, and the sensing circuitry 192c, or at least one circuit thereof, are configured as a hardware unit. All such combinations and variations are intended to fall within the scope of the present disclosure. In some embodiments, the one or more processors may be shared by multiple circuits (e.g., the pump control circuitry 192a, the valve control circuitry 192b, and the sensing circuitry 192c) may comprise or otherwise share the same processor which, in some example embodiments, may execute instructions stored, or otherwise accessed, via different areas of memory 192.

The pump control circuitry 192a is configured to receive an activation/deactivation signal to activate/deactivate the pump 142. For example, the pump control circuitry 192a may receive the activation/deactivation signal from the display 134 or the I/O device 198 to activate/deactivate the pump 142.

The valve control circuitry 192b is configured to generate a valve control signal operable to selectively move or to cause selective movement of the valve 160 between the first configuration (e.g., the first angular orientation) and the second configuration (e.g., the second angular orientation). In some embodiments, the sensing circuitry 192c may be configured to receive a sensing signal from the sensor(s) 136, for example, corresponding to a pressure inside the first internal volume V1 or a change of volume thereof. For example, the sensing circuitry 192c may be configured to receive a first sensing signal indicative of a negative pressure being exerted within the first internal volume, which corresponds to the user exhaling. The sensing circuitry 192c may communicate the first sensing signal to the valve control circuitry 192b, and responsive to the first sensing signal, the valve control circuitry 192b is configured to move the valve 160 into the first configuration (e.g., the first angular orientation) to cause air to be communicated from the outlet 146 of the pump into the first internal volume V1. Similarly, the sensing circuitry 192b may receive a second sensing signal indicative of a positive pressure being exerted within the first internal volume, which corresponds to the user U inhaling. The sensing circuitry 192c may communicate the second sensing signal to the valve control circuitry 192b, and responsive to the second sensing signal, the valve control circuitry 192b is configured to move the valve 160 into the second configuration (e.g., the second angular orientation) to cause air to be communicated out of the first internal volume V1 to the inlet 144 of the pump 142, as previously described herein.

Figure 7:
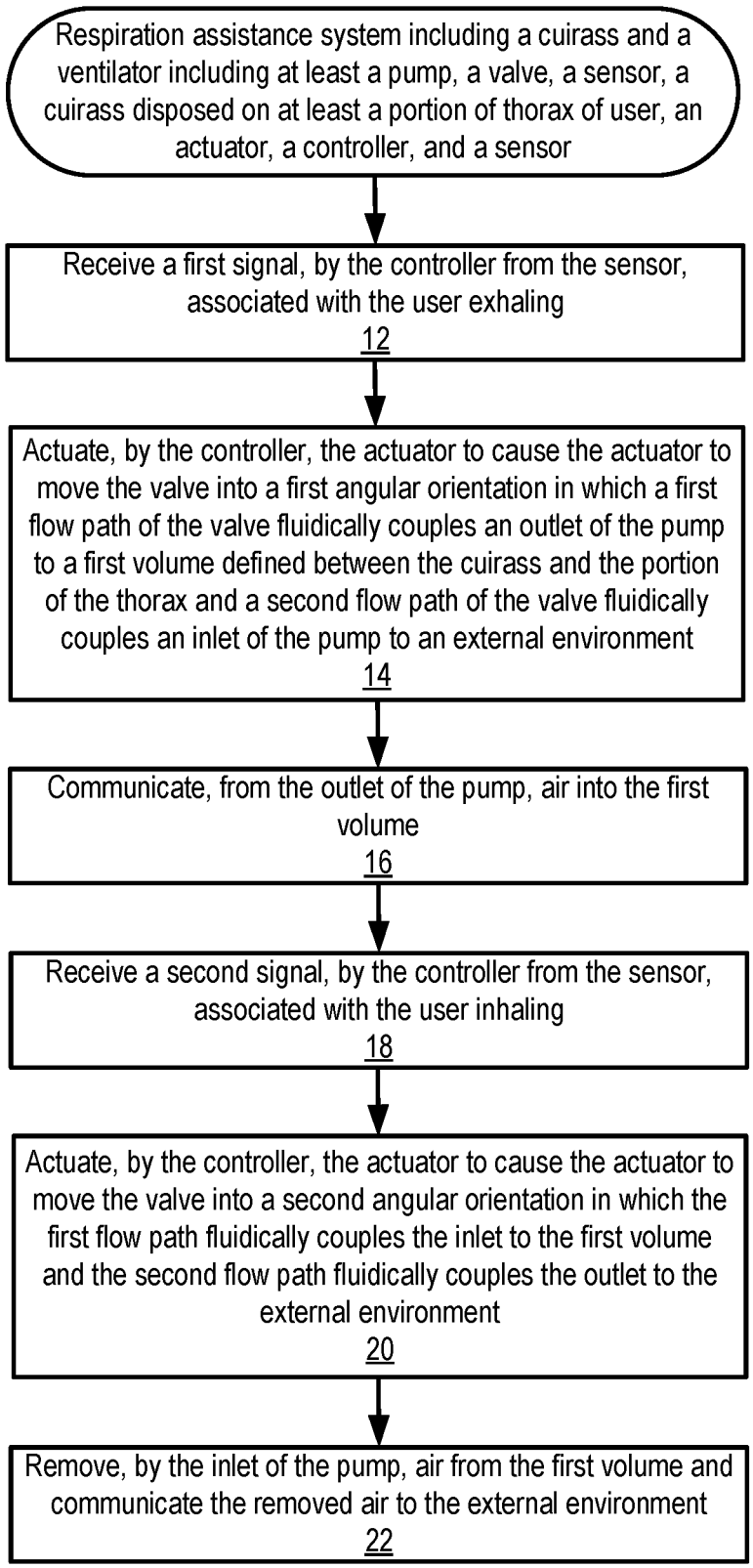
FIG. 7 is a flow chart of a method for controlling operation of a respiration assistance system that includes a cuirass, and a ventilator including at least a pump, a valve, a sensor, an actuator, and a controller, according to an embodiment.

FIG. 7 is a flow chart of a method 10 for controlling operation of a respiration assistance system (e.g., the system 100), according to an embodiment. In some implementations, for example, the respiration assistance system includes a cuirass (e.g., the cuirass 102), and a ventilator (e.g., the ventilator 130) including at least a pump (e.g., the pump 142), a valve (e.g., the valve 160), a sensor (e.g., the sensor(s) 136), an actuator (e.g., the actuator 180), and a controller (e.g., the controller 190), according to an embodiment. While described with respect to the controller 190 and the system 100, the operations of the method 10 can be performed with any controller or control unit capable of performing the operations of the method 10 to selectively provide air to, or draw air from a cuirass of any respiration assistance system. All such implementations are envisioned and should be considered to be included within the scope of the present application. The method 10 is described with reference to the controller 190 and/or the system 100 (and/or components or aspects thereof) to facilitate the understanding of one implementation and is not intended to imply that the operations of the method 10 are limited to being implemented in, on, or by the controller 190 and/or the system 100.

The method 10 includes receiving, at the controller 190 from the sensor(s) 136, a first signal associated with the user U exhaling, at 12. For example, the sensor(s) 136 (e.g., a pressure sensor) may detect a negative pressure within the first internal volume V1 of the cuirass 102 due to the user U exhaling, and generate the first signal corresponding to the positive pressure, and thus, the user U exhaling.

At 14, the actuator 180 is actuated via the controller 190 to move the valve 160 into the first angular orientation in which the first flow path 164 fluidically couples the outlet 146 of the pump 142 to the first internal volume V1 of the cuirass 102, and the second flow path 168 fluidically couples the inlet 142 to an external environment, as previously described herein. As previously described, the system 100 may also include the manifold 150 configured to be fluidically coupled to the pump 142. In such embodiments, in the first angular orientation, the first flow path 164 fluidically couples the first channel 152 to the second channel 152, and the second flow path 168 fluidically couples the third channel 156 to the fourth channel 158. At 16, the method 10 includes communicating, via the pump 142, air from the external environment into the first internal volume V1 to assist the user U in exhaling, as previously described.

At 18, the controller 190 receives from the sensor(s) 136, a second signal associated with the user U inhaling. For example, the sensor(s) 136 may detect a positive pressure within the first internal volume V1 due to the user U inhaling, and generate the second signal corresponding to the negative pressure, and thus, the user U inhaling.

At 20, the actuator 180 is actuated via the controller 190 to move the valve 160 into the second angular orientation in which the first flow path 164 fluidically couples the inlet 144 of the pump 142 to the first internal volume V1 of the cuirass 102, and the second flow path 168 fluidically couples the outlet 146 to an external environment, as previously described herein. For example, the actuator 180 can rotate the valve 160 about the central axis of the valve 160 in the first rotational direction to place the valve 160 in the first angular orientation and in a second rotational direction opposite the first rotational direction to place the valve 160 in the second angular orientation. The actuator 180 may rotate the valve 90 degrees about the central axis between the first angular orientation and the second angular orientation. Moreover, in embodiments in which the system 100 includes the manifold 150, the first flow path 164 fluidically couples the second channel 154 to the fourth channel 158, and the second flow path 168 fluidically couples the first channel 152 to the third channel 156 in the second angular orientation.

At 22, the method 10 includes communicating, via the pump 142, air from the first internal volume V1 to the external environment to further generate negative pressure within the first internal volume V1 to assist the user U in inhaling, as previously described. The operations of the method 10 may then be repeated until, for example, the user U or a caregiver deactivates the system 100.

Figure 8:
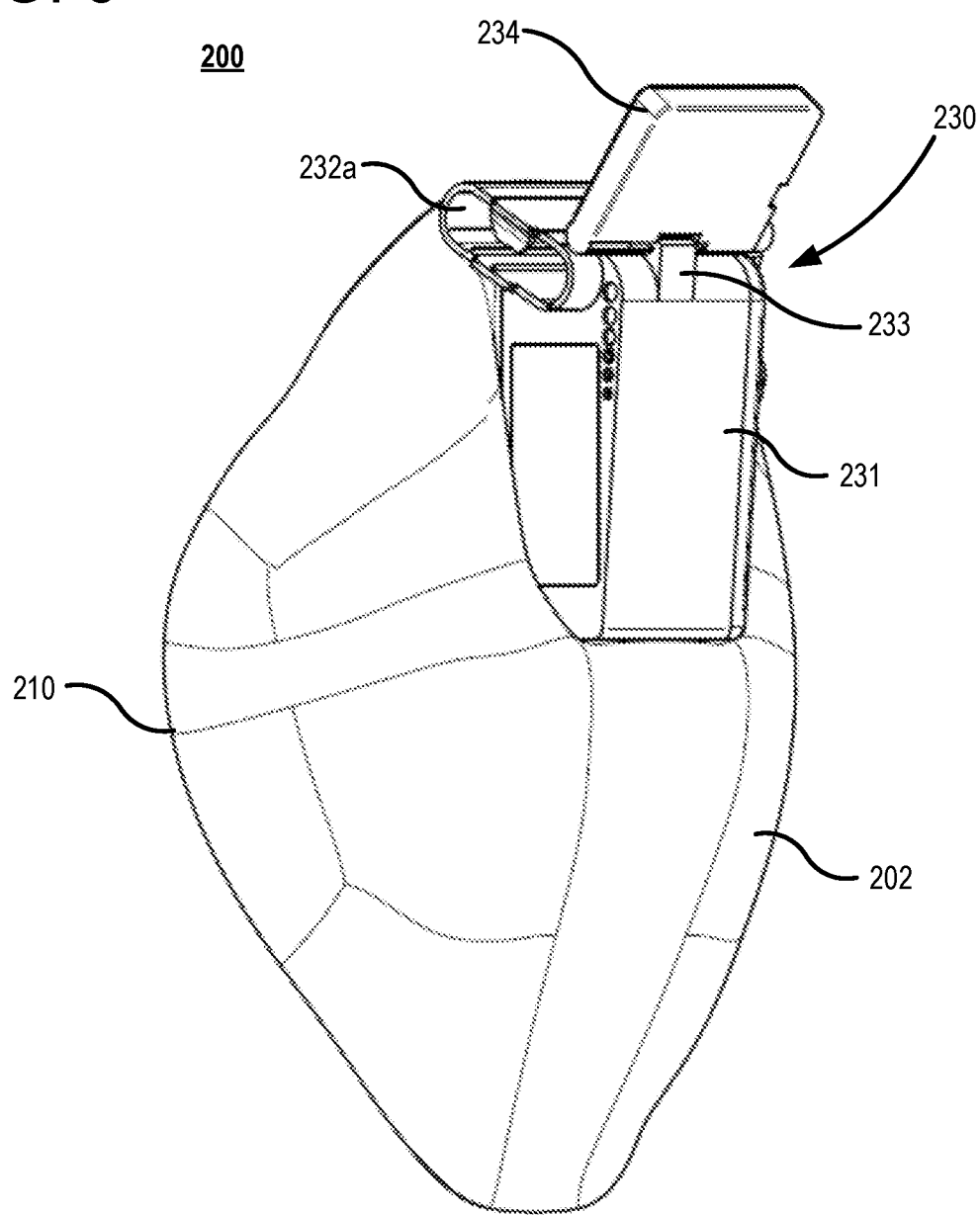
FIG. 8 is a front perspective view of a respiration assistance system that includes a cuirass and a ventilator, according to an embodiment.
Figure 9:
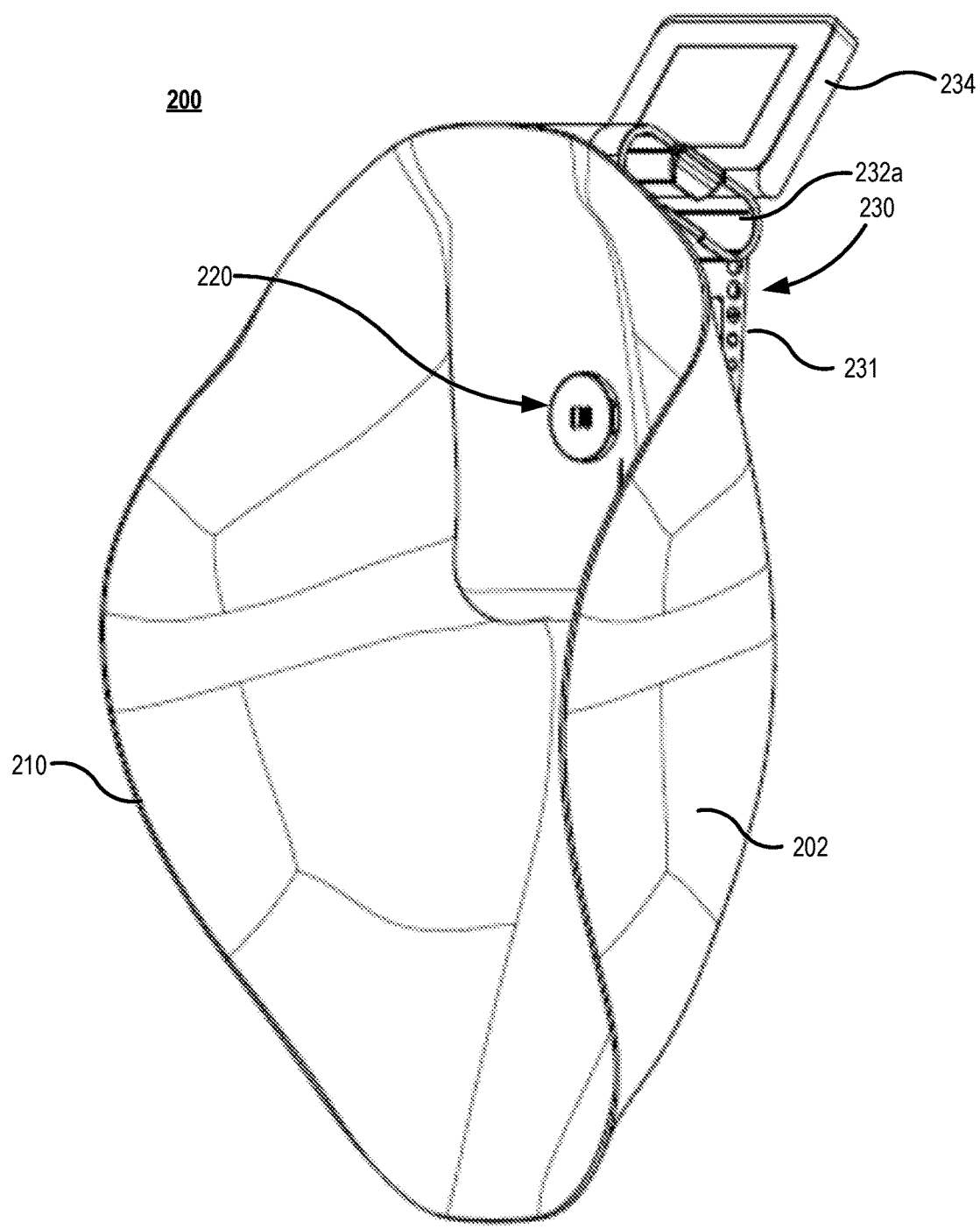
FIG. 9 is a rear perspective view of the system of FIG. 8.

FIG. 8 is a front perspective view and FIG. 9 is a rear perspective view of a respiration assistance system 200, according to an embodiment. The system 200 includes a cuirass 202 and a ventilator 230 coupled to the cuirass 202. The cuirass 202 is configured to be coupled to at least a portion of a thorax of a user (e.g., on the chest, on a portion of a chest, on an abdomen, on a portion of the abdomen, or a portion of a chest and a portion of the abdomen of the user U) such that a first internal volume is defined between a surface of the cuirass 202 and at least a portion of the thorax. A sealing member 210 is coupled along a peripheral edge of the cuirass 202 and configured to be disposed between the peripheral edge of the cuirass 202 and at least the portion of the thorax when the cuirass 202 is coupled thereto such that the sealing member 210 forms a fluid tight seal with at least the portion of the thorax or a fabric disposed on at least the portion of the thorax (e.g., a vest, shirt, blouse, or another piece of fabric being worn by the user).

In some embodiments, the sealing member 210 may be over molded over the peripheral edge of the cuirass 202. In such embodiments, the cuirass 202 may define multiple indents or through-holes proximate to the peripheral edge of the cuirass 202 and the sealing member 210 may include corresponding protrusions inserted into the through-holes, as described with respect to the system 100. In some embodiments, the sealing member 210 may be coupled to the cuirass 202 using coupling members (e.g., fasteners such as screws, nuts, bolts, rivets, clips, clamps, etc.). In some embodiments, the sealing member 210 may be friction fit to the peripheral edge of the cuirass 202. In some embodiments, the sealing member 210 may be fixedly coupled to the peripheral edge of the cuirass 202 (e.g., via adhesives, fusion bonding, thermal bonding, etc.). The sealing member 210 may be substantially similar to the sealing member 110 described with respect to the system 100 and therefore, not described in further detail herein. While not show, the system 200 may include a securement (e.g. the securement 130 or any securement described in the '740 application or the '892 application) configured to secure the cuirass 202 to the user, as previously described with respect.

The cuirass 202 has a shape or profile that may correspond to or resemble the portion of the thorax of the user on which the cuirass 202 is configured to be disposed. The cuirass 202 may be formed from a rigid or semi-rigid material (e.g., plastics, polycarbonate, polymers, any other suitable material, or a combination thereof) having the sealing member 210 coupled along a peripheral edge thereof that is shaped for engagement with at least the portion of the thorax (e.g., anterior chest and/or abdomen of the user). The cuirass 202 has a concave inner surface or face shaped so that when the sealing member 210 is engaged with the use's thorax or portion thereof, the first internal volume is formed between the inner surface of the cuirass 202 and the corresponding portion of the thorax. The first internal volume (e.g., an inflatable volume) is configured to receive air from the ventilator 230. A compressive force is exerted on the portion of the thorax of the user when air is filled into the first internal volume to assist the user in exhaling air, and a pulling force is exerted on the portion of the thorax when air is evacuated from the first internal volume to assist the user in inhaling air. In some embodiments, the cuirass 202 may be custom made to correspond to a shape of the portion of the thorax of the user, for example based on a 3D scan of the thorax or portion of the thorax of the user, as previously described. In some embodiments, the peripheral edge of the thorax may be shaped to match or mimic the curvature of the thorax of the user. By having the peripheral edge closely match the curvature of the patient's thorax, the peripheral edge of the cuirass 202 and thereby the sealing member 210 coupled thereto can fully engage the thorax, which reduces leakage of air from or to the first interior volume. In some embodiments, instead of using 3D scanning, the peripheral edge can be an approximate of the curves of the thorax of the user.

In some embodiments, the cuirass 202 may be made of a transparent or semi-transparent material. The transparent or semi-transparent cuirass 202 may provide the benefit of allowing optical sensors that are not mounted within the cuirass 202 to obtain measurements within the first interior volume (e.g., temperature measurements, pressure measurements, etc.). Moreover, having a transparent cuirass 202 may allow a caregiver such as a doctor to observe the thorax of the user while the user is wearing the cuirass 202. In some embodiments, the cuirass 202 may be made of an opaque material. In some embodiments, the cuirass 202 may be made of an opaque material and include transparent or semi-transparent portions (e.g., windows).

Figure 10:
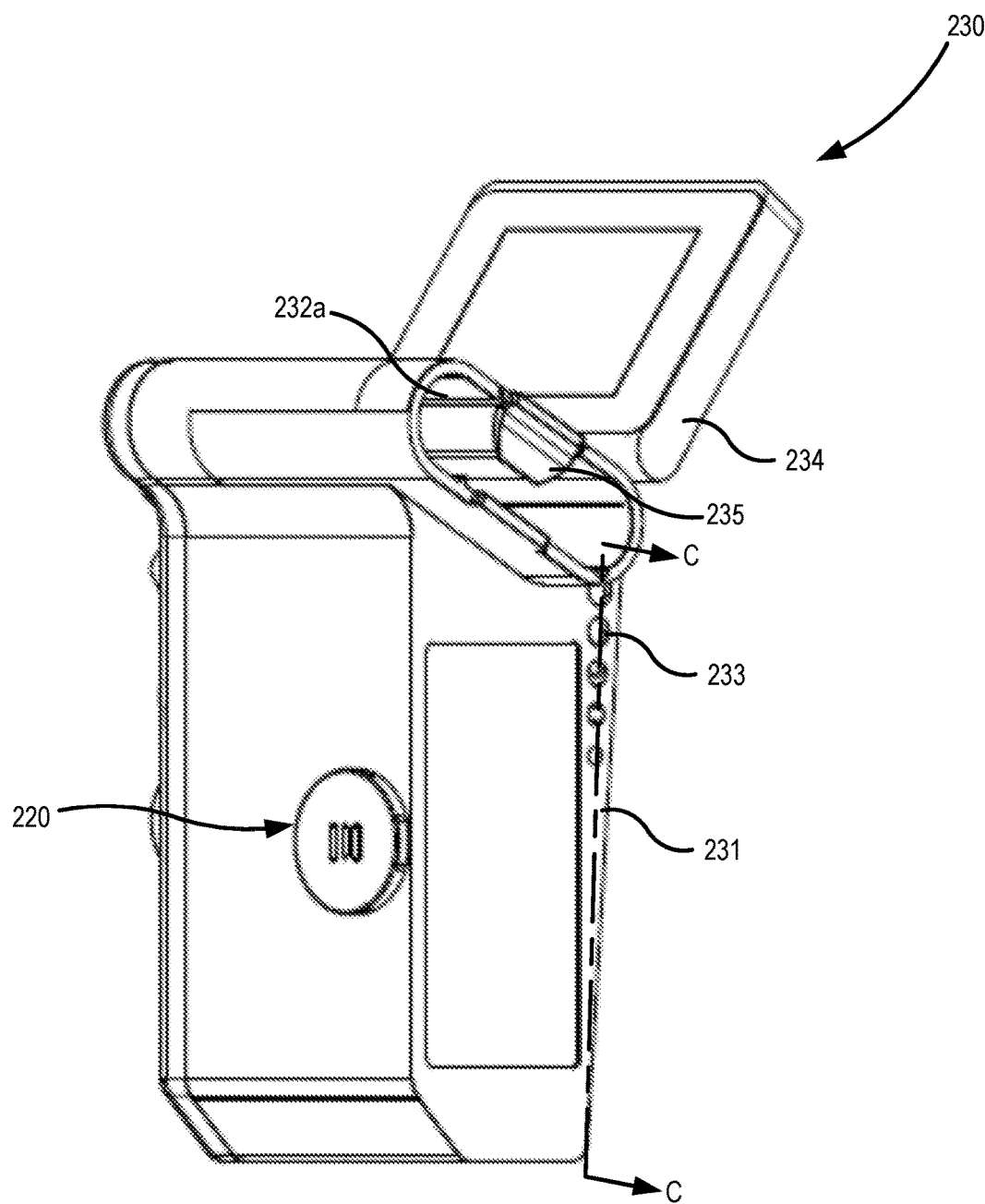
FIG. 10 is a rear perspective view of the ventilator included in the system of FIG. 8.
Figure 11A:
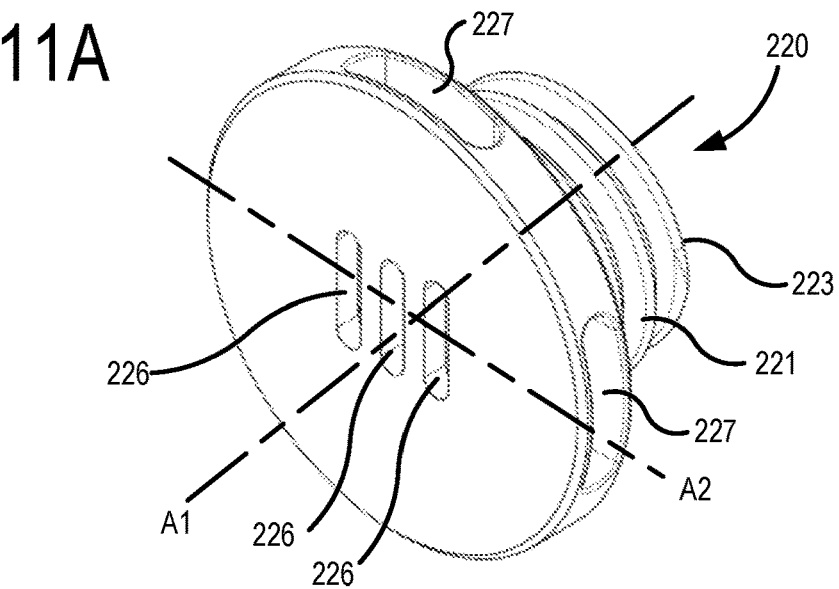
FIG. 11A is a rear perspective view of a flow member that fluidically couples the ventilator of the system of FIG. 8 to the cuirass.
Figure 11B:
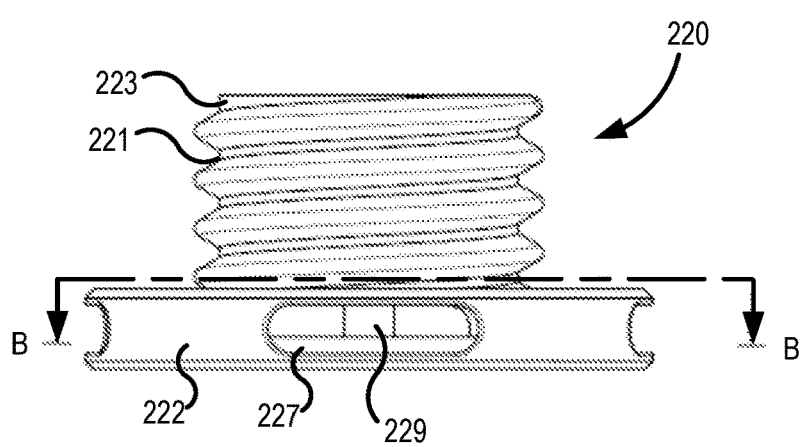
FIG. 11B is a side view of the flow member.
Figure 11C:
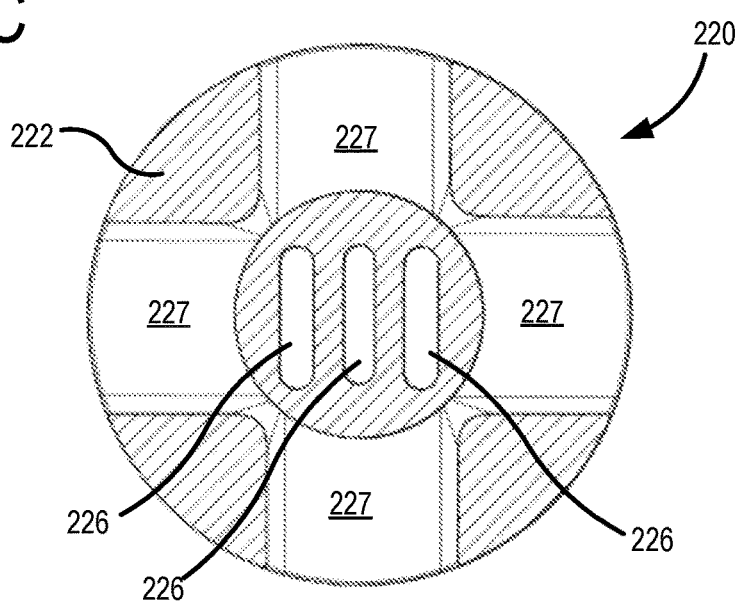
FIG. 11C is a cross-section view of the flow member taken along the line B-B in FIG. 11B.

FIG. 10 is a rear perspective view of the ventilator 230 included in the system 200 of FIG. 8. The cuirass 202 can also define an aperture therethrough, for example, on a portion of the cuirass 202 that faces the ventilator 230 through which at least a portion of flow member 220 is disposed for fluidically coupling the cuirass 202 to the ventilator 230. FIG. 11A is a rear perspective view of the flow member 220 that fluidically couples the ventilator 230 of the system 200 to the cuirass 202. FIG. 11B is a side view of the flow member 220, and FIG. 11C is a cross-section view of the flow member 220 taken along the line B-B in FIG. 11B. As shown in FIGS. 11A-11C, the flow member 220 includes a first portion 221 having a first end 223 coupled to the ventilator 230 (e.g., a second channel 254 of a manifold 250 included in the ventilator 230 as described herein) and a second end 222 disposed through the aperture into the first volume of the cuirass 202.

As shown in FIG. 9, the flow member 220 includes a second portion 222 disposed on an inner surface of the cuirass 202 within the first internal volume. The second portion 222 has a cross-sectional width that is larger than a cross-sectional width (e.g., diameter) of the aperture such that once the first portion 221 is coupled to the ventilator 230, a wall of the cuirass 202 is secured or clamped between the second portion 222 and the ventilator 230 (e.g., a corresponding wall of a housing 231 of the ventilator 230 shown in FIG. 10), thereby securing the cuirass 202 to ventilator 230. In some embodiments, a gasket or any other sealing member may be disposed between the inner surface of the cuirass 202 and a corresponding surface of the second portion 222 so as to fluidically seal the first internal volume from an external environment located outside the internal volume.

The flow member 220 defines one or more axial flow channels extending through the flow member 220 from the first portion 221 to the second portion 222. The one or more of axial flow channels fluidically couple the ventilator 230 to the first internal volume. Multiple slots 226 are defined a proximate end of the one or more axial flow channels, which is located within the first internal volume. The multiple slots 226 may serve as diffusers to diffuse the flow of air entering or exiting the first internal volume to facilitate uniform distribution of the air into the first internal volume, and may also serve to suppress a noise level of the air traveling to or from the internal volume so as to increase user comfort. In some embodiment, each slot 226 may correspond to a single axial flow channel.

The second portion 222 of the flow member 220 also defines a set of second flow channels 227 oriented at an angle that is orthogonal to the one or more axial flow channels extending through the flow member 220. For example, the one or more axial flow channels may be oriented along a first axis A1 that runs along a longitudinal axis of the first portion 221, and the one or more second flow channels 227 may extend along a second axis A2 that is oriented at an angle of about 90 degrees with respect to the first axis A1 as shown in FIG. 11A. While FIG. 11C shows the second portion 222 defining 4 second flow channels that are radially spaced apart from each other by an angle of about 90 degrees, the flow member 220 can include any number of second flow channels 227.

The second flow channels 227 may provide additional flow paths for fluidically coupling the first internal volume to the one or more axial flow channels. One or more openings 229 are defined in a wall of the one or more axial channels to fluidically couple the second channels 227 to the one or more first axial channels. The second channels 227 may provide an alternate flow path to spread the air as it is communicated from the ventilator 230 to the first internal volume, for example, to allow rapid, controlled, and/or uniform filling of the first internal volume with air during exhalation. The second flow channels 227 may also lower resistance for air to be communicated out of the first internal volume, as well as more uniformly draw the air out of the first internal volume so as to allow a more uniform suction force to be exerted on the thorax during inhalation by the user.

Figure 12:
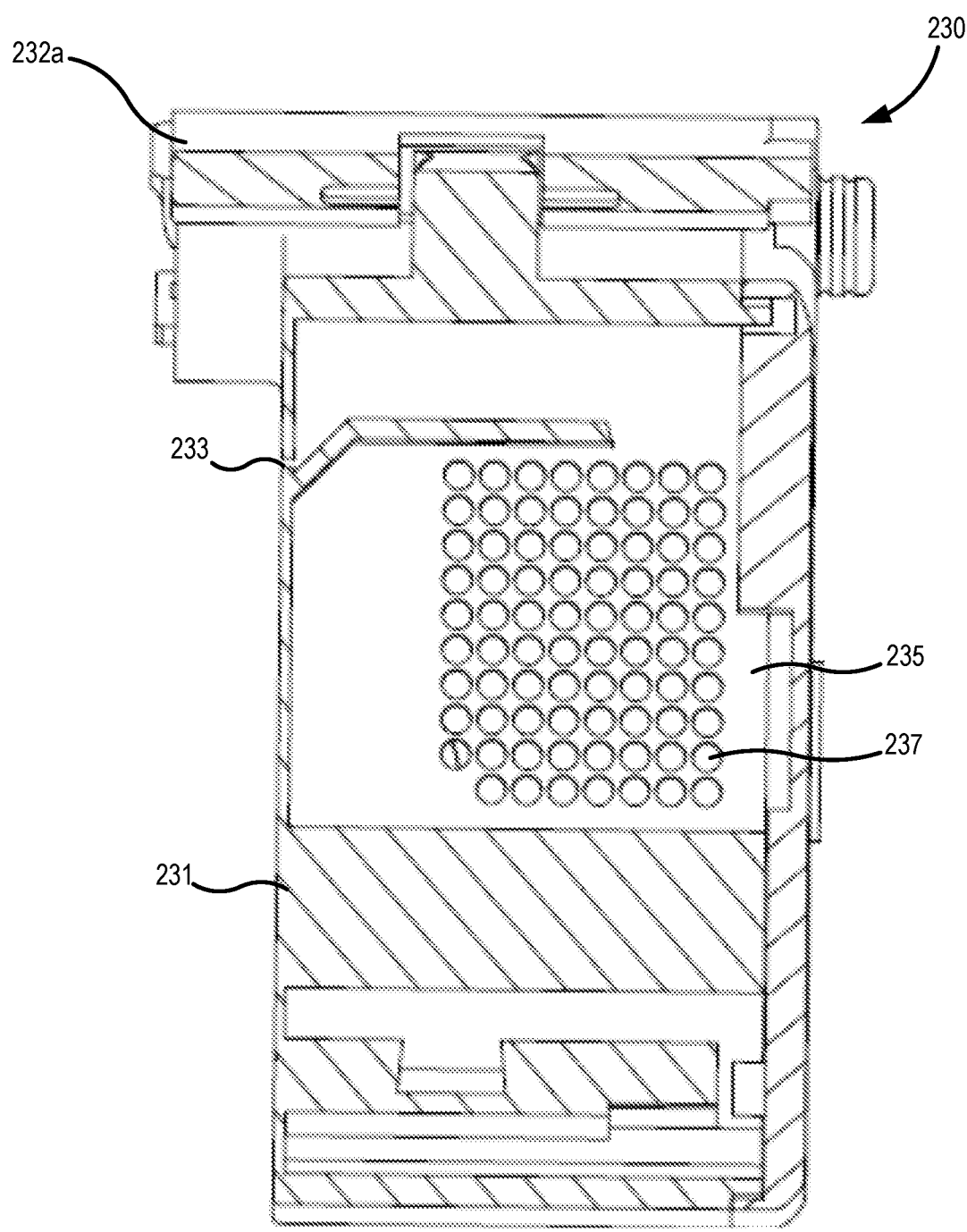
FIG. 12 is a cross-section view of a housing of the ventilator taken along the line C-C in FIG. 10.

Referring also to FIGS. 12-16, the ventilator 230 may include the housing 231, a pumping assembly 240 including a pump 242, a valve 260, an actuator 280, a manifold 272, a gasket 276, a controller 290, a power supply receptacle 232a, and a display 234. The ventilator 230 includes a housing 231 defining a second internal volume within which various components of the ventilator 230 are disposed. FIG. 12 is a cross-section view of a housing 231 of the ventilator taken along the line B-B in FIG. 10. The housing 231 defines a set of openings 233 to allow air to flow into an out of the second internal volume. While FIGS. 10 and 12 show the set of openings 233 as having a circular shape, the set of openings 233 may have any suitable shape (e.g., circular, oval, elliptical, square, rectangular, polygonal, any other suitable shape or combination thereof) and/or size (e.g., diameter) to allow air to flow into and out of the second internal volume.

As shown in FIG. 12, the housing 231 includes a wall 235 disposed in the second internal volume and separating the second internal volume into a first portion that is fluidically coupled to an external environment through the set of openings 233, and a second portion within which the components of the ventilator 230 are disposed. The wall 235 defines multiple openings 237 therethrough through which air can pass between the first portion and the second portion of the second internal volume. In some embodiments, the multiple openings 237 may cause the wall 235 to serve as a muffler or silencer configured to reduce a sound level as air passes between the first portion and the second portion. In some embodiments, an aperture may be defined in the sidewall of the housing 231 through which the flow member 220 is coupled to the ventilator 230.

The power supply receptacle 232a is configured to removably receive a power supply (e.g., the power supply 132) that is configured to store electrical power and provide electrical power to various components of the ventilator 230 (e.g., the pump 242, the actuator 280, the controller 290, and/or the display 234). The power supply may be substantially similar to the power supply 132 described with respect to the system 100, and therefore not described in further detail herein. In some embodiments, solar panels may be provided on the ventilator 230 to convert solar energy into electrical energy for charging the power storage device of the power supply.

The display 234 is disposed on and coupled to the housing 231 such that the display 234 is viewable to the user when the cuirass 202 and thereby, the ventilator 230 is disposed on the thorax of the user. The display 234 can be hingedly coupled to housing 231 such that the user can selectively rotate the display 234 into a first orientation in which the display 234 is disposed away from the housing 231 when the user intends to view or engage the display 234, and rotate the display 234 into a second orientation in which the display 234 is proximate to the housing 231 (e.g., folded flat against a surface of the housing 231 or disposed in a corresponding receptacle defined in the housing 231 when the user does not intend to engage the display 234). In some embodiments, the display 234 may be configured to automatically turn OFF (e.g., go into hibernation mode) when the display 234 is in the second orientation, and to automatically turn ON when display 234 is moved into the first orientation. The display 234 may be substantially similar in structure and function to the display 134 described with respect to the system 100 and therefore, not described in further detail herein.

Figure 13:
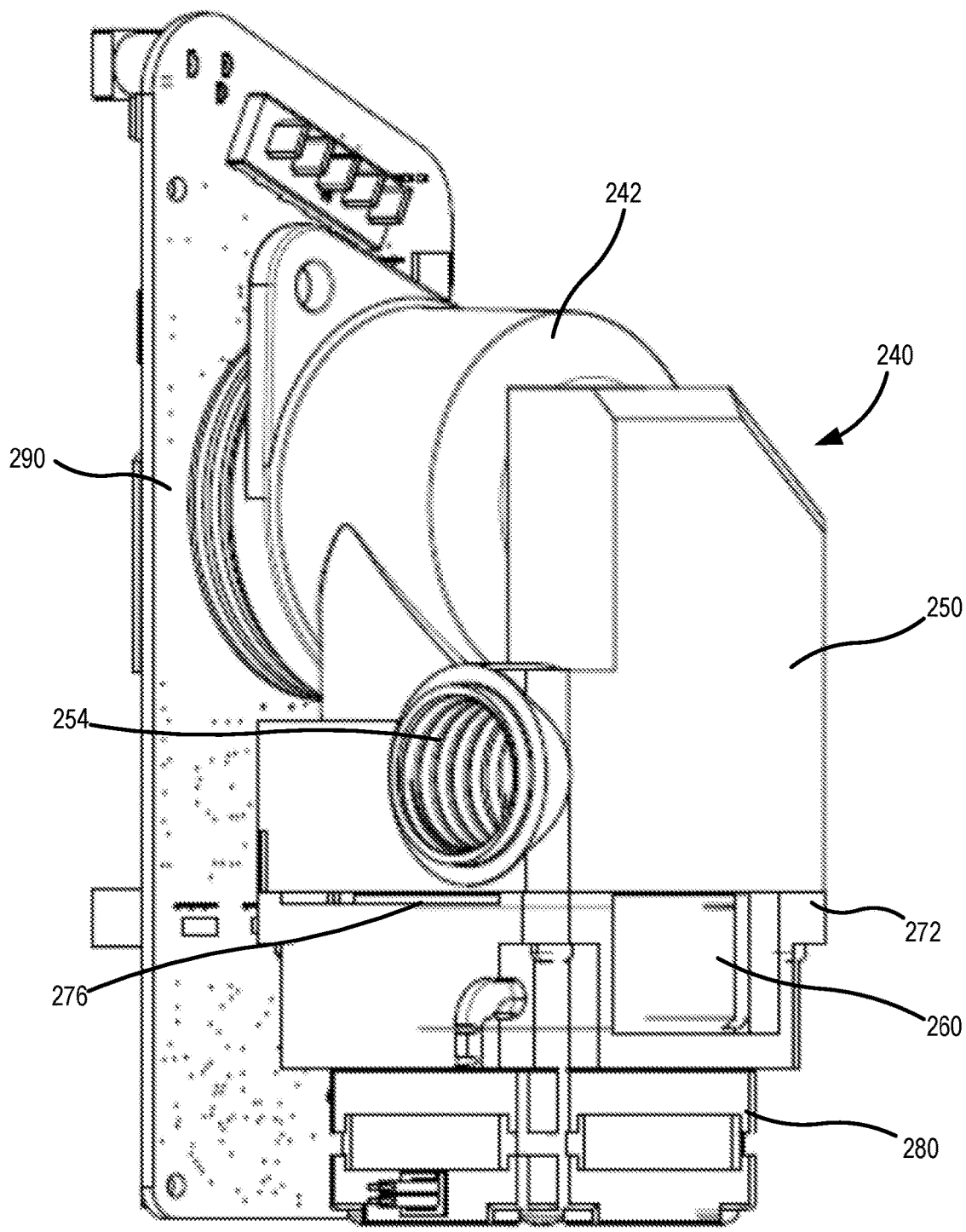
FIG. 13 is a rear perspective view of the ventilator of FIG. 10 with the housing of the ventilator removed to show a controller and a pumping assembly including pump, a manifold, a valve body, a valve, and a motor, which are disposed within an internal volume of the housing.
Figure 14:
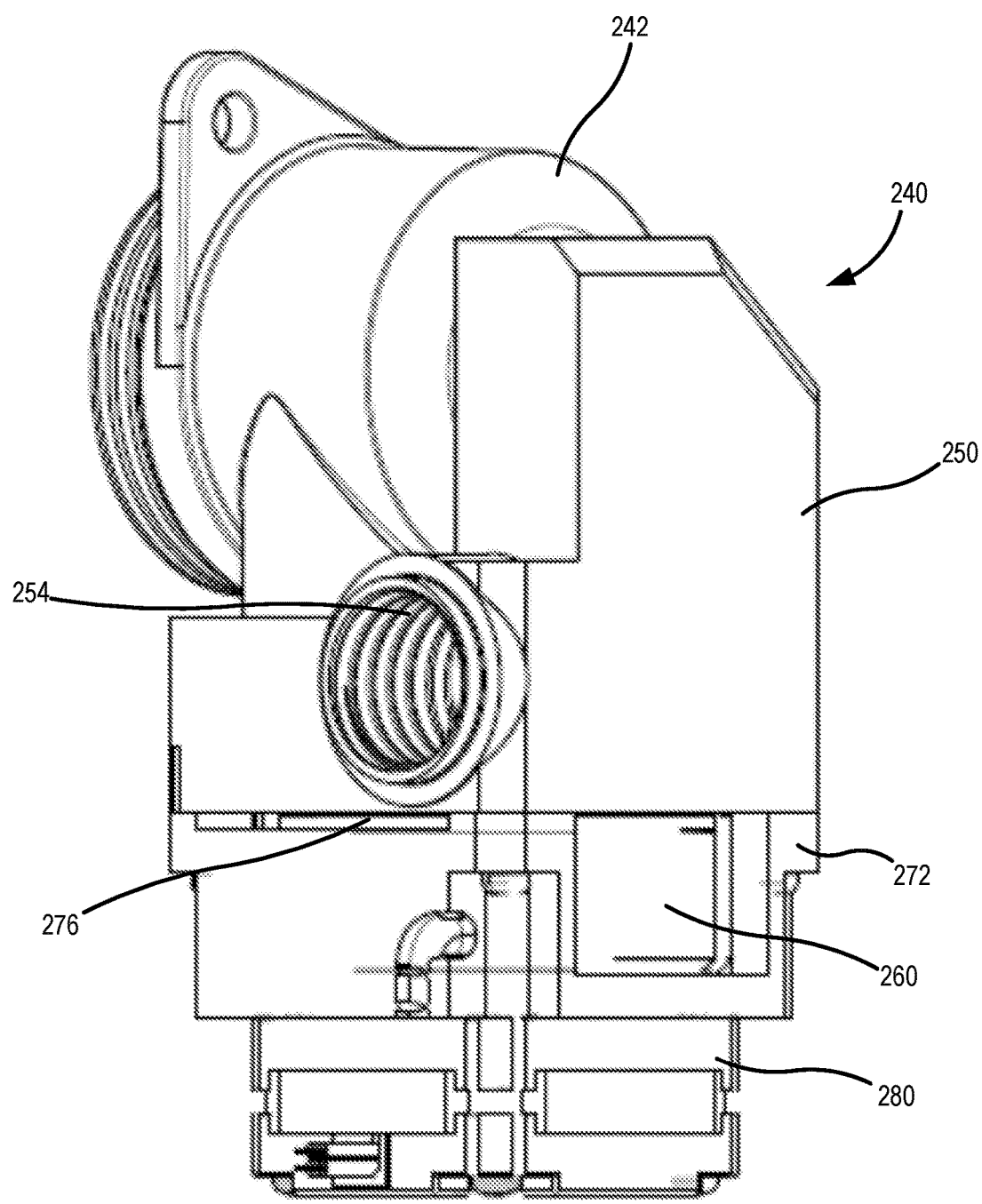
FIG. 14 is a rear perspective view of the pumping assembly of FIG. 13.
Figure 15:
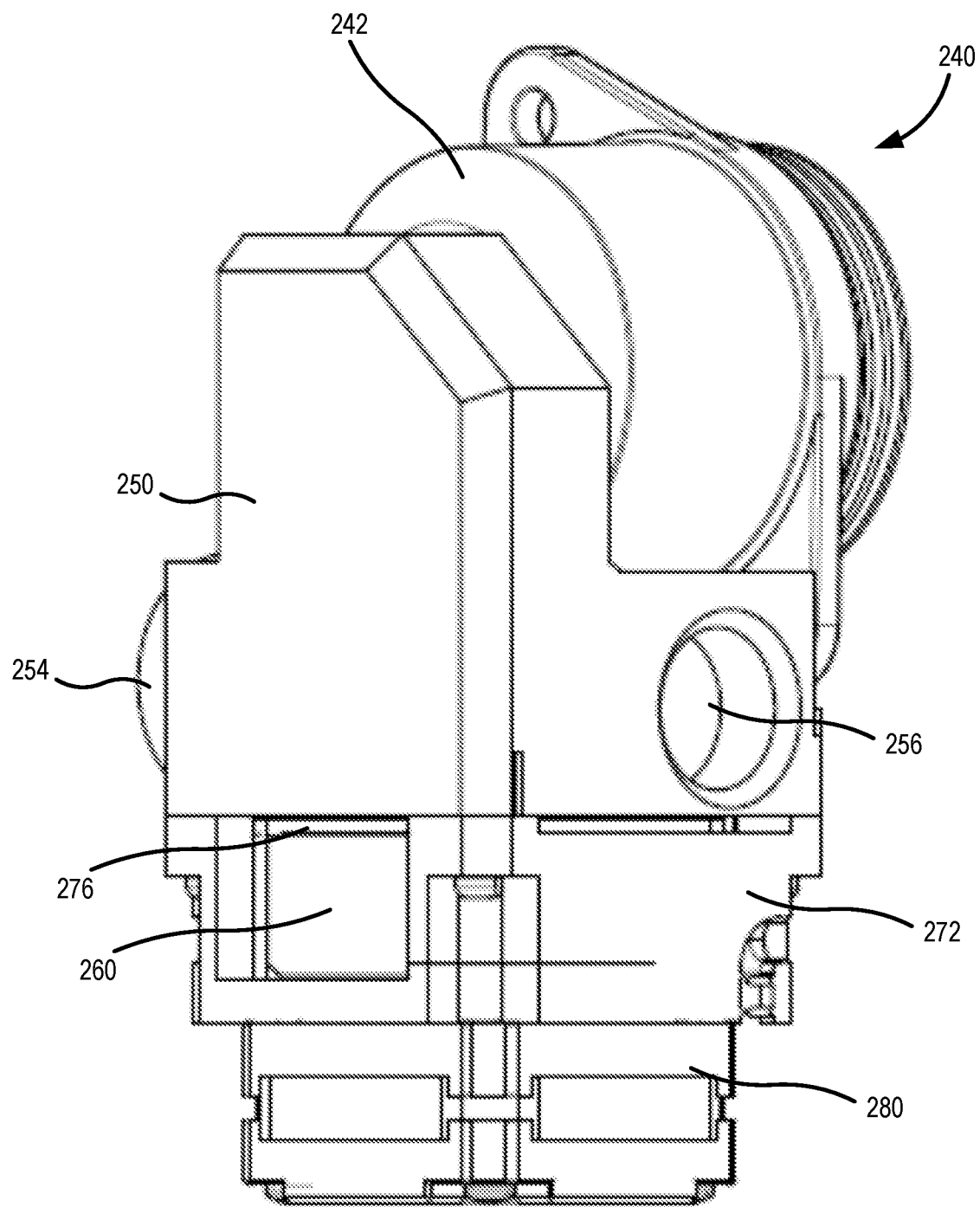
FIG. 15 s a front perspective view of the pumping assembly of FIG. 14.
Figure 16:
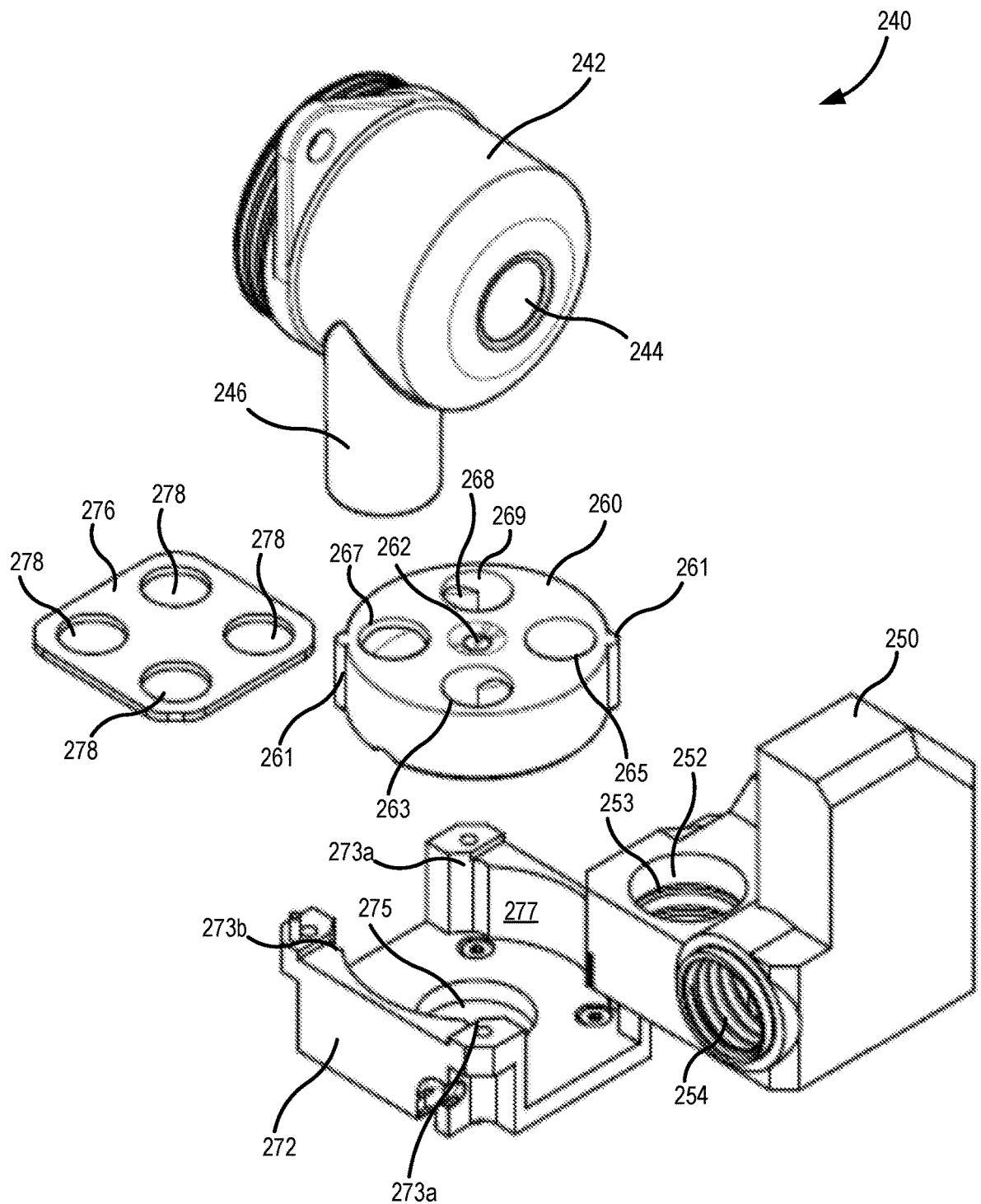
FIG. 16 is an exploded rear perspective view of the pumping assembly of FIG. 14.

FIG. 13 is a rear perspective view of the ventilator 230 of FIG. 10 with the housing 231 of the ventilator 230 removed to show the controller 290 and the pumping assembly within the internal volume of the housing. FIG. 14 is a rear perspective view, FIG. 15 s a front perspective view, and FIG. 16 is an exploded rear perspective view of the pumping assembly 240. As shown in FIG. 13, the controller 290 is in communication with the actuator 280 and may also be in communication with the pump 242, and/or the display 234. The controller 290 is configured to control the operations of the ventilator 230. For example, the controller 290 may be configured to activate the pump 242 (e.g., based on an input received from the user such as via the display 234), determine a pressure within the first internal volume based on a pressure signal received from a sensor (e.g., the sensor(s) 136), and/or control operation of the actuator 280 to move the valve 260 between the first configuration (e.g., the first angular orientation) and the second configuration (e.g., the second angular orientation).

For example, the controller 290 may be determine that the user is exhaling (e.g., based on a pressure signal received from the sensor(s) 136) and responsive to the determining that the user is exhaling, cause the actuator 280 to move the valve 260 into the first angular orientation. Moreover, the controller 290 may determine that the user is inhaling (e.g., based on a pressure signal from the sensor(s) 136), and responsive to determining that the user is inhaling, cause the actuator 280 to move the valve 260 into the second angular orientation. The controller 290 may be substantially similar in structure and function to the controller 190 described with respect to FIGS. 3 and 6 and therefore, not described in further detail herein. While not shown, the ventilator 230 may include one or more sensors configured to measure one or more parameters of the ventilator 230 and/or the user. The one or more sensors may be substantially similar to the sensor(s) 136 described with respect to the system 100 and therefore, not described in further detail herein.

As shown in FIGS. 13-16, the ventilator 230 includes a pumping assembly 240 that includes the pump 242, the manifold 250, the valve 260, a valve body 272, a gasket 276, and the actuator 280. The pump 242 includes an inlet 244 configured to draw or suck air into the pump 242, and an outlet 246 configured to expel pressurized air out the pump 242. The pump 242 may include a centrifugal pump or a blower, as shown in FIGS. 13-16. However, any other suitable pump may be used, for example, a peristaltic pump, a vacuum pump, a diaphragm pump, any other suitable pump, or a combination thereof.

The manifold 250 can be removably or fixedly coupled to the pump 242, for example, via fasteners such as screws, nuts, bolts, rivets, etc., or via a snap-fit or friction-fit connection, clips, clamps, any other suitable connection, or a combination thereof. For example, as shown in FIG. 16, the manifold 250 defines a first channel 252 within which at least a portion of the outlet 246 of the pump 242 is inserted. In some embodiments, an O-ring 253 or any other sealing member may be disposed on an inner radial surface of a wall of the first channel 252, for example, within a groove defined therein. In such embodiments, when the outlet 246 is at least partially disposed within the first channel 252, the O-ring 253 contacts an outer surface of the outlet 246 to form a substantially fluid tight seal, and optionally, friction fit the outlet 246 within the first channel 252 so as to physically as well as fluidically couple the pump 242 to the manifold 250.

In some embodiments, the manifold 250 may include a single piece that is molded, casted, or machined so as to define multiple channels in the manifold 250. As previously described, the manifold 250 includes the first channel 252 that is fluidically coupled to the outlet 246 of the pump 242. The manifold 250 also defines a second channel 254 fluidically coupled to the first internal volume defined by the cuirass 202. The second channel 254 defines coupling features such as, for example, threads as shown in FIG. 16 that are configured to mate with mating threads defined on the first portion 221 of the flow member 220 to physically and fluidically couple the flow member 220 to the second channel 254. In some embodiments, at least a portion of the second channel 254 may extend radially out of the housing 231 towards the aperture defined in the housing 231, and may abut against an inner surface of the wall of the housing 231 in which the aperture 239 is defined or extend out of the aperture 239 for coupling to the flow member 220. In such embodiments, a gasket or O-ring may be disposed between the second channel 254 and the corresponding wall of the housing 231 to fluidically seal the aperture. In some embodiments, the flow member 230 (e.g., the first portion 221 of the flow member 220) may extend into the second internal volume of the housing 231 and be coupled to the second channel 254. In such embodiments, the gasket or O-ring may be disposed between a surface of the flow member 220 (e.g., a distal surface of the second portion 222) and an outer surface of the wall of the housing 231.

The manifold 250 also defines a third channel 256 fluidically coupled to a volume external to the manifold 250, i.e., the second internal volume of the housing 231 and through the openings 233 of the housing 231 to the environment external to the housing 231. Moreover, the manifold 250 defines a fourth channel 258 fluidically coupled to the inlet 244 of the pump 242 (FIG. 17C-17D). The fourth channel 258 may define a second receptacle in which at least a portion of the inlet 244 is received.

The valve 260 is disposed in the second internal volume and configured to be moved between a first angular orientation during exhalation in which the outlet 246 of the pump 242 is fluidically coupled to the first internal volume and the inlet 244 of the pump 242 is coupled to the second internal volume via the valve 260, and a second angular orientation in which the outlet 246 of the pump 242 is fluidically coupled to the second internal volume and the inlet 244 of the pump 242 is fluidically coupled to the first internal volume via the valve 260. The valve 260 includes a rotational valve having a generally circular profile or shape. The valve 260 is configured to rotate about a central axis CA thereof between the first angular orientation and the second angular orientation. For example, as described in FIG. 16, the valve 260 defines a central channel 262 configured to receive at least a portion of a shaft 281 (FIG. 17C) of the actuator 280 (e.g., a motor such as a stepper motor, a linear motor, a servo motor, any other suitable motor) such that the valve 260 is coupled to and rotationally locked with the shaft 281 such that rotation of the shaft 281 of the actuator 280 causes the valve 260 to rotate between the first angular orientation and the second angular orientation about the central axis CA. In some embodiments, the shaft 281 may include a flat portion inserted within a corresponding flat portion of the central channel 262 of the valve 260 to rotationally lock the valve 260 to the shaft 281 of the actuator 280.

The actuator 280 may be configured to move the valve 260 in a first angular direction (e.g., a clockwise direction) to move the valve 260 into the first angular orientation, and in a second angular direction opposite to the first angular direction (e.g., an anticlockwise direction) to move the valve 260 into the second angular orientation. In some embodiments, the actuator 280 rotates the valve 260 approximately 90 degrees about the central axis between the first angular orientation and the second angular orientation. In some embodiments, instead of moving the valve 260 in opposite rotational directions to move the valve 260 between the first angular orientation and the second angular orientation, the actuator 280 may be configured to move the valve 260 in the same rotational direction to move the valve 260 between the first and second angular orientations about the central axis CA. For example, the actuator 280 may rotate the valve 260 in one of a clockwise or anticlockwise direction (e.g., by an angle of about 90 degrees) to move the valve 260 into the first angular orientation (e.g., during exhaling by the user). The actuator 280 may then rotate the valve 260 in the same one of the clockwise or anticlockwise direction (e.g., by an angle of about 90 degrees) to move the valve 260 into the second angular orientation about the central axis CA, and so on and so forth. In such embodiments, the actuator 280 may include, for example, a stepper motor is configured to rotate the valve 260 in predetermined steps to move the valve 260 between the first and second angular orientations.

The valve 260 include a first flow path 264 and a second flow path 268 such that in the first configuration (e.g., the first angular orientation) of the valve 260, the first flow path 264 fluidically couples the outlet 246 of the pump to an inlet of the cuirass 202 (e.g., the flow member 220) and thus the first internal volume, and the second flow path 268 fluidically couples the inlet 244 of the pump 242 to the external environment through the second internal volume. The first flow path 264 fluidically couples a first opening 263 defined by the valve 260 to a second opening 265 defined by the valve 260. Moreover, in the second configuration (e.g., the second angular orientation) of the valve 260, the first flow path 264 fluidically couples the inlet 244 to the inlet of the cuirass 202 and thus the first internal volume, and the second flow path 268 fluidically couples the outlet 246 to the external environment through the second internal volume as described in further detail herein. The second flow path 268 fluidically couples a third opening 267 defined by the valve 260 to a fourth opening 269 defined by the valve 260. Each of the first opening 263, the second opening 265, the third opening 267, and the fourth opening 269 are defined on a single planar surface of the valve 260, for example, a surface that faces the pump 242. The valve 260 may include a single piece formed via forging, casting, machining, any other suitable method, or any suitable combination thereof.

As shown in FIG. 16, the first flow path 264 and the second flow path 268 are disposed parallel to each other, for example, located on either side of the central axis of the valve 260 and at about the same distance from the central axis. Moreover, the first flow path 264 and the second flow path 268 may have about the same length such that the first opening 263, the second opening 265, the third opening 267, and the fourth opening 269 are located at about the same radial distance from the central axis CA. Thus, the valve 260 is structured such that the first flow path 264 and the second flow path 268 extend along a first direction (e.g., along one of an X-axis or a Y-axis) parallel to each other in the first angular orientation, and extend along a second direction that is about perpendicular to the first direction (e.g., the other one of the X-axis or the Y-axis) in the second angular orientation.

The pumping assembly 240 may also include a valve body 272 within which the valve 260 is disposed. As shown in FIGS. 16 and 17A, the valve body 272 has an interior surface defining a cavity 277 such that the valve 260 is movably disposed in the cavity 277 between the first angular orientation and the second angular orientation. The cavity 277 has a shape that corresponds to a shape of the valve 260 such that the valve 260 is snugly disposed in the cavity 277 while having sufficient clearance between the interior surface of the valve body 272 and a corresponding exterior surface of the valve 260 to enable the valve 260 to move freely within the cavity 277 between the first and second angular orientations. An aperture 275 is defined in a base of the cavity 277 to allow the shaft 281 of the actuator 280 to be disposed therethrough into the central channel 262 into the valve 260.

The interior surface of the valve body 272 defines a pair of first notches 273a and a pair of second notches 273b offset from the set of first notches 273a, for example, offset by an angle of about 90 degrees. Moreover, the valve 260 has a set of projections 261 protruding from an outer radial surface thereof and radially offset from each other by an angle of about 180 degrees. The pair of first notches 273a and the pair of second notches 273b are located such that the projections 261 are at least partially disposed in the corresponding one of the first notches 273a when the valve 260 is in the first angular orientation and at least partially disposed in the corresponding one of the second notches 273b when the valve 260 is in the second angular orientation. The projections 261, and the first notches 273a and second notches 273b may serve as a motion stops to limit the motion of the valve 260 as it rotates between the first and second angular orientations to ensure proper alignment of the valve 260 with the manifold 250, as described herein.

The gasket 276 is disposed between the valve 260 and the manifold 250. The gasket 276 can be configured to form a seal between the valve 260 and the manifold 250 in each of the first angular orientation and the second angular orientation of the valve 260. For example, the gasket 276 may include a flat sheet of a resilient material (e.g., rubber, silicone, polymers, ceramics, any other suitable material, or a combination thereof) that defines a plurality of through-holes 278 that correspond to the locations of the first opening 263, the second opening 265, the third opening 267, and the fourth opening 269, respectively. The first opening 243, the second opening 265, the third opening 267, and the fourth opening 269 may defined symmetrically about a central axis of the valve 260 (e.g., located at the same radial distance from the central axis of the of the valve 260, and radially spaced apart at an angle of about 90 degrees from each other). Thus, each of the first opening 263, the second opening 265, the third opening 267, and the fourth opening 269 is axially aligned with one of the plurality of through-holes of the gasket 276 in each of the first and second angular orientations.

Figure 17B:
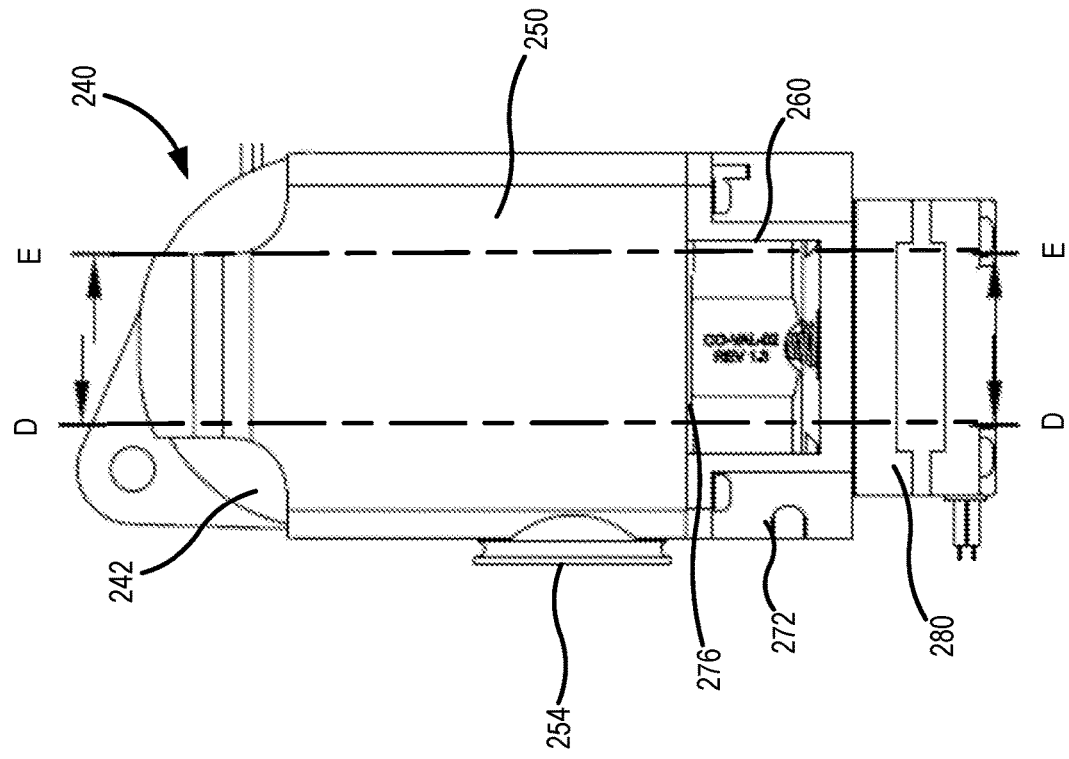
FIG. 17B is a rear perspective view of the pumping assembly in an assembled configuration with the valve being in the first angular orientation.
Figure 17A:
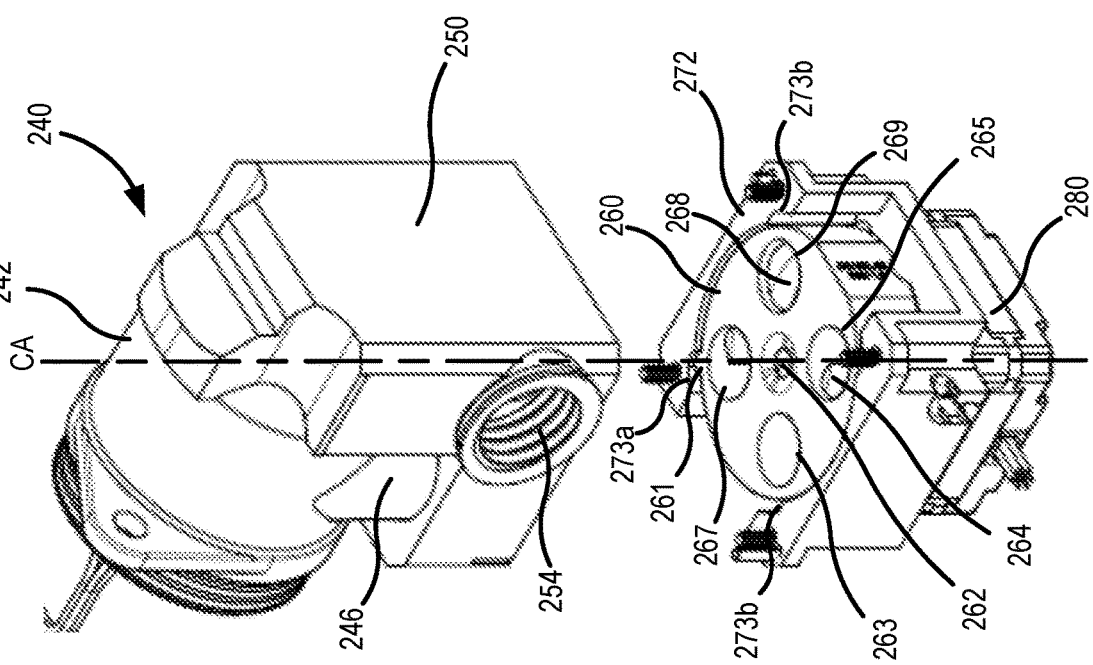
FIG. 17A is a partial exploded rear perspective view of the pumping assembly with the valve included therein being in a first angular orientation.

FIG. 17A is a partial exploded rear perspective view of the pumping assembly 240 with the valve 260 included therein being in a first angular orientation and FIG. 17B is a rear perspective view of the pumping assembly 240 in an assembled configuration with the valve 260 being in the first angular orientation. FIGS. 17C and 17D are rear cross-section views of the pumping assembly 240 of FIG. 17B taken along the lines D-D and E-E in FIG. 17B, respectively.

In the first angular orientation as shown in FIG. 17B, the valve 260 is oriented by the actuator 280 (e.g., based on a command or instruction received from the controller 290) by the rotating the valve 260 in the first rotational direction (e.g., the clockwise direction) such that projections 261 of the valve 260 are disposed in the corresponding first notches 273a of the valve body 272. Moreover, as shown in FIG. 17C, the first opening 263 is axially aligned with the first channel 252, the second opening 265 is axially aligned with the second channel 254, the third opening 267 is axially aligned with the third channel 256, and the fourth opening 269 is axially aligned with the fourth channel 258. Thus, in the first angular orientation, the first flow path 264 fluidically couples the first channel 252 and the thereby, the outlet of the pump 246 to the second channel 254 and thereby, the first internal volume of the cuirass 202.

Furthermore, as shown in FIG. 17D the second flow path 268 fluidically couples the third channel 256 and thereby, the second internal volume to the fourth channel 258 and thereby the inlet 244. Thus, in the first angular orientation which corresponds to the user exhaling, a positive pressure is applied on the first internal volume because of the outlet 246 being fluidically coupled to thereto. In the first angular orientation, air flows from outside the housing 231 through the second internal volume into the inlet 244 via the fourth channel 258, the second flow path 268, and the third channel 256, respectively, and then into the first internal volume of the cuirass 202 from the outlet 246 via the first channel 252, the first flow path 264, and the second channel 254, respectively. Thus, positive pressure is applied on at least a portion of the thorax of the user to which the cuirass 202 is coupled to assist the user in exhaling air out of the user's lungs.

Figure 18A:
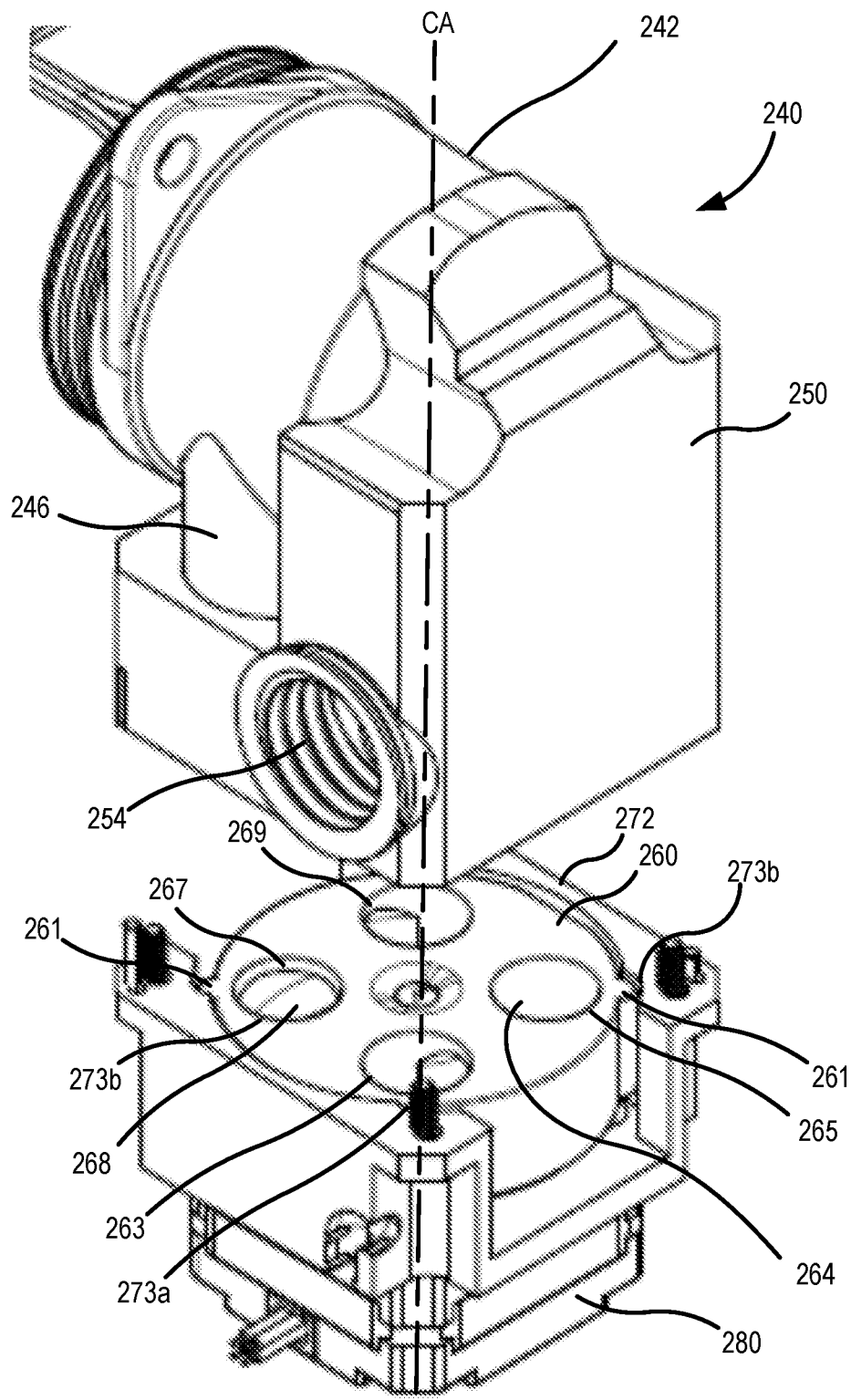
FIG. 18A is a partial exploded rear perspective view of the pumping assembly with the valve being in a second angular orientation.

FIG. 18A is a partial exploded rear perspective view, and FIG. 18B is a partially exploded front perspective view of the pumping assembly 240 with the valve 260 in the second angular orientation. FIG. 18C is a rear view of the pumping assembly of FIG. 18B in an assembled configuration, and FIGS. 18D and 18E are side cross-section views of the pumping assembly 240 of FIG. 18C taken along the lines F-F and G-G in FIG. 18C, respectively.

In the second angular orientation shown in FIGS. 18A-18E, the valve 260 is oriented by the actuator 280 (e.g., based on a command or instruction received from the controller 290) by the rotating the valve 260 in the second rotational direction (e.g., the anticlockwise direction) such that projections 261 of the valve 260 are disposed in the corresponding second notches 273b of the valve body 272. The projections 261 and the first and second notches 273a and 273b may serve as motion limiters or motion stops to inhibit the actuator 280 from moving the valve 260 beyond the desired first or second angular orientations, and may also serve as alignment features to ensure the openings 263, 265, 267, and/or 269 of the valve 260 are axially aligned with corresponding one of the channels 252, 254, 256, and/or 258, as described herein.

In the second angular orientation, the first opening 263 is now axially aligned with the second channel 254, the second opening 265 is axially aligned with the fourth channel 258 as shown in FIG. 18D. Moreover, the third opening 267 is axially aligned with the first channel 252, and fourth opening 269 is axially aligned with the third channel 256 as shown in FIG. 18E. Thus, in the second angular orientation, the first flow path 264 fluidically couples the second channel 253 and thereby, the first internal volume of the cuirass 202 to the fourth channel 258, and thereby the inlet 244 of the pump 242. Furthermore, the second flow path 268 fluidically couples the first channel 252 and thereby, the outlet 246 of the pump 242 to the third channel 256 and thereby, the second internal volume and therethrough, the external environment outside the housing 231.

Thus, in the second angular orientation which corresponds to the user inhaling, a negative pressure is applied on the first internal volume because of the inlet 244 being fluidically coupled to thereto, thus applying a suction force on the portion of the thorax of the user on which the cuirass 202 is disposed to assist the user in inhaling. In the second angular orientation, air flows from the first internal volume via the second channel 254, the first flow path 264 and the fourth channel 258 into the pump inlet 244, thereby removing air from the first internal volume. Moreover, air flows from the outlet 246 of the pump 242 through the first channel 252, the second channel 254, and the third channel 256 to the second internal volume and subsequently, out of the housing 231.

The present technology is not limited in its application to the details of construction and the arrangement of components set forth in the preceding description or illustrated in the drawings. The present technology is capable of other embodiments and of being practiced or of being carried out in various ways. Also, the phraseology and terminology used herein is for the purpose of description and should not be regarded as limiting.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The arrangements described herein have been described with reference to drawings. The drawings illustrate certain details of specific arrangements that implement the systems, methods and programs described herein. However, describing the arrangements with drawings should not be construed as imposing on the disclosure any limitations that may be present in the drawings.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and It should be understood that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes, and omissions may also be made in the design, operating conditions, and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, an FPGA, an ASIC, and/or the like. Software modules (executed on hardware) can be expressed in a variety of software languages (e.g., computer code), including C, C++, Java™, Ruby, Visual Basic™, Python™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools, and/or combinations thereof (e.g., Python™). Additional examples of computer code include, but are not limited to, control signals, encrypted code, and compressed code.

What is claimed:

1. A system, comprising
a cuirass configured to be coupled to at least a portion of at least one of a thorax or abdomen of a user such that a first internal volume is defined between a surface of the cuirass and at least the portion of the at least one of the thorax or abdomen;
a ventilator coupled to the cuirass so as to be outside of and in fluid communication with the first internal volume, the ventilator comprising:
a housing defining a second internal volume and at least one opening to allow air to flow into or out of the housing;
a pump disposed in the second internal volume, the pump including an inlet and an outlet;
a valve disposed in the second internal volume, the valve defining a first flow path and a second flow path therethrough;
an actuator operatively coupled to the valve; and
a controller in communication with the actuator, the controller configured to:
responsive to determining that the user is exhaling, cause the actuator to move the valve into a first configuration in which the first flow path fluidically couples the outlet to the first internal volume and the second flow path fluidically couples the inlet to second internal volume, and
responsive to determining that the user is inhaling, cause the actuator to move the valve into a second configuration in which the first flow path fluidically couples the inlet to the first internal volume and the second flow path fluidically couples the outlet to the second internal volume,
wherein the housing includes a wall disposed in the second internal volume, the wall separating the second internal volume into a first portion that is fluidically coupled to an external environment through the at least one opening of the housing, and a second portion within which the pump, the valve, and the actuator are disposed, the wall defining a plurality of openings configured to reduce a sound level as air passes between the first portion and the second portion.

2. The system of claim 1, wherein the first configuration is a first angular orientation and the second configuration is a second angular orientation, the actuator configured to rotate the valve about a central axis in a first rotational direction to place the valve in the first angular orientation and in a second rotational direction opposite the first rotational direction to place the valve in the second angular orientation.

3. The system of claim 1, wherein the first flow path fluidically couples a first opening defined by the valve to a second opening defined by the valve and the second flow path fluidically couples a third opening defined by the valve to a fourth opening defined by the valve, each of the first opening, the second opening, the third opening, and the fourth opening being defined on a single planar surface of the valve.

4. The system of claim 1, further comprising:
a manifold coupled to the pump, the manifold defining:
a first channel fluidically coupled to the outlet,
a second channel configured to be fluidically coupled to the first internal volume when the cuirass is coupled to the at least one of the thorax or abdomen of the user,
a third channel fluidically coupled to a volume external to the manifold, and
a fourth channel fluidically coupled the inlet.

5. The system of claim 1, further comprising:
a valve body having an interior surface defining a cavity, the valve being movably disposed in the cavity between the first configuration and the second configuration,
the interior surface of the valve body forming a first notch and a second notch offset from the first notch, and
the valve having a projection formed on a surface thereof, the projection at least partially disposed in the first notch when the valve is in the first configuration and at least partially disposed in the second notch when the valve is in the second configuration.

6. The system of claim 1, wherein the first configuration is a first orientation relative to the pump and the second configuration is a second orientation relative to the pump, the controller is further configured to:
cause the actuator to move the valve to a third orientation relative to the pump, the third orientation being between the first orientation and the second orientation such that at least one of the first flow path or the second flow path is in fluid communication with each of the inlet and the outlet of the pump.

7. The system of claim 1, further comprising:
a sealing member coupled along a peripheral edge of the cuirass and configured to be disposed between the peripheral edge of the cuirass and at least the portion of the at least one of the thorax or abdomen when the cuirass is coupled thereto such that the sealing member forms a fluid tight seal with at least the portion of the at least one of the thorax or abdomen, or a fabric disposed on at least the portion of the at least one of the thorax or abdomen.

8. The system of claim 7, wherein the sealing member forms a skirt extending from the peripheral edge of the cuirass within the first internal volume, the sealing member being formed of relatively soft and flexible material allowing the sealing member to form the fluid tight seal with at least the portion of the at least one of the thorax or abdomen, or the fabric disposed on at least the portion of the at least one of the thorax or abdomen while the user is inhaling and while the user is exhaling.

9. A method for controlling an ambulatory respiration assistance system that includes a cuirass configured to be coupled to at least one of a thorax or abdomen of a user such that a volume is defined between an internal surface of the cuirass and the at least one of the thorax or abdomen, and a ventilator physically and fluidically coupleable to the cuirass, the ventilator having a housing, a pump, a valve, an actuator coupled to the valve, and a controller, the method comprising:
receiving, at a controller of the ventilator and from a sensor, a first signal associated with the user exhaling;
actuating the actuator via the controller to move the valve into a first angular orientation in which a first flow path of the valve fluidically couples an outlet of the pump to the volume and a second flow path of the valve fluidically couples an inlet of the pump to an external environment;
communicating, via the pump, air from the external environment into the volume;
receiving, at the controller and from the sensor, a second signal associated with the user inhaling;
actuating the actuator via the controller to rotate the valve into a second angular orientation in which the first flow path fluidically couples the inlet of the pump to the volume and the second flow path fluidically couples the outlet of the pump to the external environment; and
communicating, via the pump, air from the volume to the external environment,
wherein the housing includes a wall separating an internal volume of the housing into a first portion that is fluidically coupled to an external environment through at least one opening of the housing, and a second portion within which the pump, the valve, and the actuator are disposed, the wall defining a plurality of openings configured to reduce a sound level as air passes between the first portion and the second portion.

10. The method of claim 9, wherein the sensor is at least one of a pressure sensor, a flow sensor, a strain gauge, or an acoustic sensor.

11. The method of claim 9, wherein the actuator rotates the valve about a central axis of the valve in a first rotational direction to place the valve in the first angular orientation and in a second rotational direction opposite the first rotational direction to place the valve in the second angular orientation.

12. The method of claim 11, wherein the actuator rotates the valve 90° about the central axis between the first angular orientation and the second angular orientation.

13. The method of claim 9, wherein the volume is a first volume, the respiration assistance system further includes a manifold fluidically coupled to the pump, the manifold defining:
a first channel fluidically coupled to the outlet of the pump;
a second channel configured to be fluidically coupled to the first volume when the cuirass is coupled to the at least one of the thorax or abdomen of the user;
a third channel fluidically coupled to a second volume external to the manifold; and
a fourth channel fluidically coupled to the inlet of the pump.

14. The method of claim 13, wherein:
in the first angular orientation, the first flow path fluidically couples the first channel to the second channel, and the second flow path fluidically couples the third channel to the fourth channel, and
in the second angular orientation, the first flow path fluidically couples the second channel to the fourth channel, and the second flow path fluidically couples the first channel to the third channel.

15. The method of claim 9, wherein the first flow path fluidically couples a first opening defined by the valve to a second opening defined by the valve and the second flow path fluidically couples a third opening defined by the valve to a fourth opening defined by the valve, each of the first opening, the second opening, the third opening, and the fourth opening being defined on a single planar surface of the valve.

\* \* \* \* \*